US008321008B2

(12) United States Patent  
Petersen et al.

(10) Patent No.: US 8,321,008 B2  
(45) Date of Patent: Nov. 27, 2012

(54) COMBINATION CARTRIDGE AND DEVICE FOR ELECTROKINETIC DELIVERY OF MEDICAMENT TO A TREATMENT SITE

(75) Inventors: John S. Petersen, Acton, MA (US); Dennis I. Goldberg, Sudbury, MA (US); James W. Kelland, East Walpole, MA (US); Paul K. Rand, Roystone (GB); Anthony Patrick Charles Jones, Much Hadham (GB); Robert W. Etheredge, Natick, MA (US)

(73) Assignee: Nitric Biotherapeutics, Inc., Bristol, PA (US)

( * ) Notice: Subject to any disclaimer, the term of this patent is extended or adjusted under 35 U.S.C. 154(b) by 466 days.

(21) Appl. No.: 11/565,360

(22) Filed: Nov. 30, 2006

(65) Prior Publication Data

US 2007/0233048 A1    Oct. 4, 2007

Related U.S. Application Data

(60) Provisional application No. 60/740,678, filed on Nov. 30, 2005.

(51) Int. Cl.  
*A61N 1/30* (2006.01)  
*A61N 1/00* (2006.01)

(52) U.S. Cl. ........... 604/20; 607/115; 607/145; 607/150

(58) Field of Classification Search .................. 604/19, 604/134, 20–22, 890.1, 891.1, 892.1, 501, 604/110, 18, 16, 533; 24/580.1, 584.1, 652, 24/704.1, 575; 607/115, 145, 149, 150  
See application file for complete search history.

(56) References Cited

U.S. PATENT DOCUMENTS

| | | | | |
|---|---|---|---|---|
| 5,562,607 A * | 10/1996 | Gyory | ............................ | 604/20 |
| 6,895,271 B2 * | 5/2005 | Henley | .......................... | 604/20 |
| 2002/0161324 A1 * | 10/2002 | Henley et al. | ................... | 604/20 |
| 2004/0133164 A1 * | 7/2004 | Funderburk et al. | .......... | 604/134 |
| 2006/0189961 A1 * | 8/2006 | Miyahara | ...................... | 604/535 |
| 2007/0185515 A1 * | 8/2007 | Stout | ............................. | 606/181 |

* cited by examiner

*Primary Examiner* — Matthew F Desanto  
(74) *Attorney, Agent, or Firm* — Riverside Law LLP

(57) ABSTRACT

A device for electrokinetic delivery of medicament to a treatment site includes a cartridge having an active electrode and a membrane overlying the active electrode and a medicament or a medicament and an electrically conductive carrier therefor, carried by the membrane in electrical contact with the electrode. The electrode opens through a surface of the cartridge remote from the membrane for connection with an electrical connector carried by the device. An locking element releasably couples the cartridge to the housing.

19 Claims, 25 Drawing Sheets

COMBINATION CARTRIDGE AND DEVICE FOR ELECTROKINETIC DELIVERY OF MEDICAMENT TO A TREATMENT SITE

BACKGROUND

This application claims the benefit of the Nov. 30, 2005 filing date of U.S. Provisional Application 60/740,678 (NV 3589-81) the entirety of which is incorporated by reference. This application is also related to concurrently filed U.S. patent application Ser. No. 11/565,335 entitled "An Applicator Cartridge For An Electrokinetic Delivery System For Self Administration Of Medicaments", the entirety of which application is incorporated by reference.

The present invention relates generally to the electrokinetic mass transfer of substances into tissue, such as an apparatus for electrokinetically delivering substances, e.g., a medicament to a treatment site on skin. The invention particularly relates to a coupling-locking mechanism between a cartridge carrying the medicament and a hand-held or finger mounted device that releases the cartridge and provides electrical power to the cartridge.

Electrokinetic delivery of medicaments for applying medication locally through an individual's skin to a treatment site is known. One type of electrokinetic delivery mechanism is iontophoresis, i.e., the application of an electric field to the skin to enhance the skin's permeability. An iontophoresis device delivers various ionic agents, e.g., ions of salts or other drugs, to the treatment site. In certain situations, iontophoretic, transdermal and transmucal cutaneous delivery techniques have obviated the need for hypodermic injection of many medicaments thereby eliminating the concomitant problem of trauma, pain and risk of infection to the individual typically associated with hypodermic injection.

Other types of electrokinetic delivery mechanisms include electroosmosis, electroporation, electromigration and endosmose, any or all of which are more generally known as electrotransport, electromolecular transport or iontophoretic methods, or more generally known as electrokinetic methods. Prior electrokinetic devices for delivering medicaments to a treatment site were typically cumbersome, bulky, costly and oftentimes required the presence of an individual at a doctor's office or treatment center and use of medical professionals to administer the medicament. More recently, devices have been developed for the private self administration of medicaments or for diagnostic application by the individual at non-medical or non-professional facilities. For example, U.S. Pat. No. 6,792,306 discloses an electrokinetic delivery device which includes a housing containing a power source, electronics and a counter electrode, the device being shaped and configured for releasable securement to an individual's finger and terminating in an applicator head having an active electrode. By applying the head to the skin overlying the treatment site and with the medicament or a medicament and a carrier therefor carried by the applicator head, the medicament may be electrokinetically delivered to the treatment site. There has developed a need for a disposable applicator cartridge which can be readily and easily manufactured at low cost and which sealingly contains the medicament whereby the cartridge can be releasably secured to the cartridge applicator device by a locking element and released, preferably ejected from a finger mounted electrokinetic medicament delivery device.

SUMMARY

A novel electrokinetic delivery system has been developed for self-administration of a medicament to a treatment site on an individual comprising a device for releasable securement to the individual's finger and shaped in part to conform to at least a portion of the individual's finger, a retainer for releasably securing the device to the individual's finger, a self-contained power source and a tactile electrode carried by the device, and a cartridge for releasable securement to the device. The cartridge may include an active electrode in electrical contact with the power source when the cartridge is secured to the device. Upon application of the active electrode to the treatment site with a medicament interposed between the active electrode and the treatment site, an electrical circuit is completed through the active electrode, the medicament or a conductive carrier therefor, the treatment site, the individual's body, the tactile electrode and the power source. The device causes an electrical circuit to flow for electrokinetically driving the medicament from the cartridge into the treatment site, which is typically on the skin of the individual.

In another embodiment, there is provided an electrokinetic delivery system for self-administration of a medicament to a treatment site on an individual comprising carrying a self-contained power source and a tactile electrode, a cartridge for releasable securement to the device, a locking element carried by one of the device and the cartridge and engaged with a locking surface on the other of the device and cartridge, and the locking element being movable to release the securement between the device and the cartridge enabling release of the cartridge from the device. The device and cartridge include a surface(s) co-operable with the locking element, enabling a bias of the element to forcibly eject the cartridge from the device. The cartridge may include an active electrode in electrical contact with the power source. When the cartridge is secured to the device and upon application of the active electrode to the treatment site with a medicament interposed between the active electrode and the treatment site, an electrical circuit is completed through which current flows. The current passes through the active electrode, the medicament or a conductive carrier therefor, the treatment site, the individual's body, the tactile electrode and the power source. The device causes an electrical circuit to flow for electrokinetically driving the medicament from the cartridge into the treatment site.

DETAILED DESCRIPTION

Figure 1:
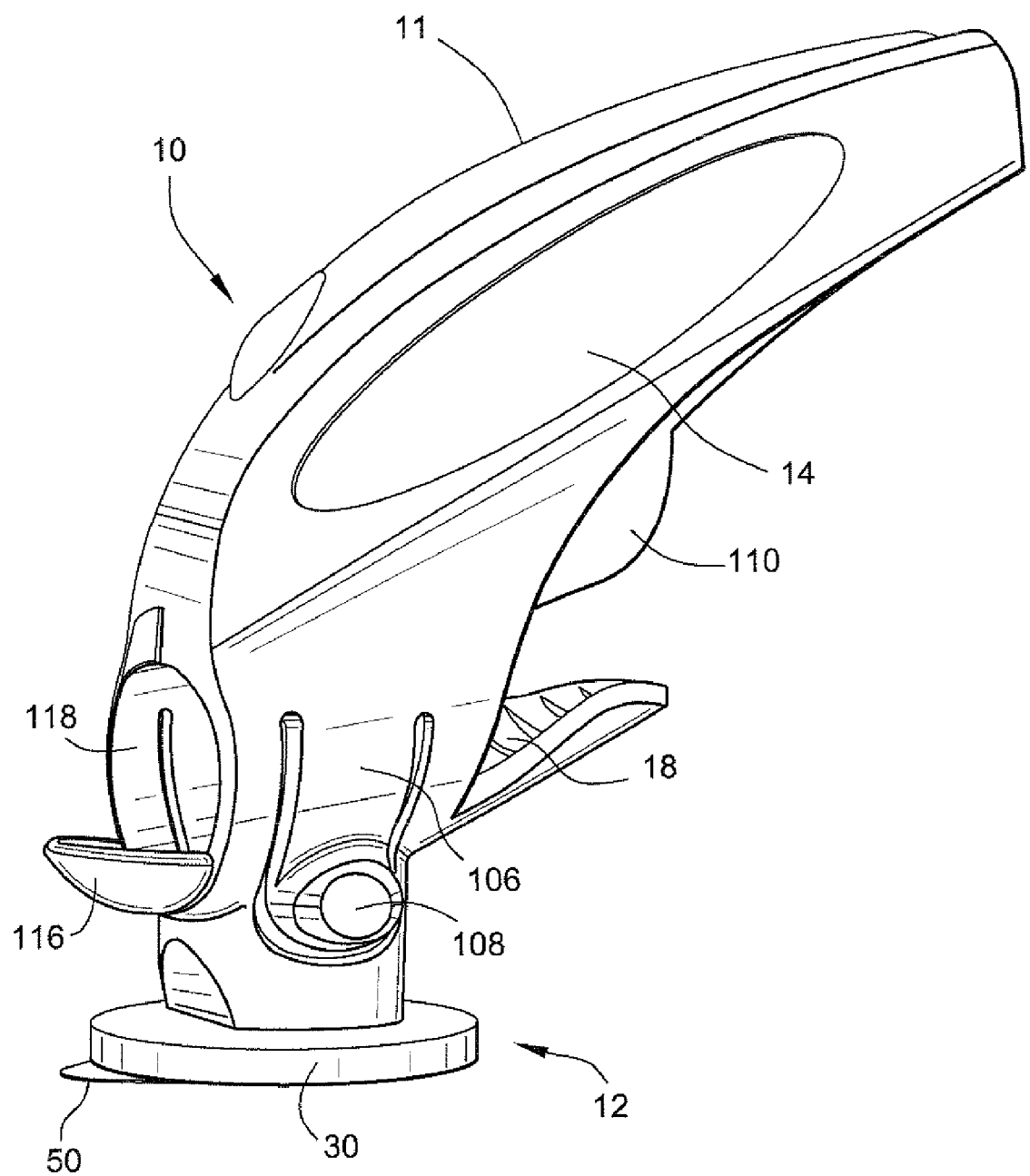
FIG. 1 is a perspective view of a first embodiment of the electrokinetic delivery device including an applicator or cartridge (collectively a "cartridge") releasably secured to the delivery device.
Figure 2:
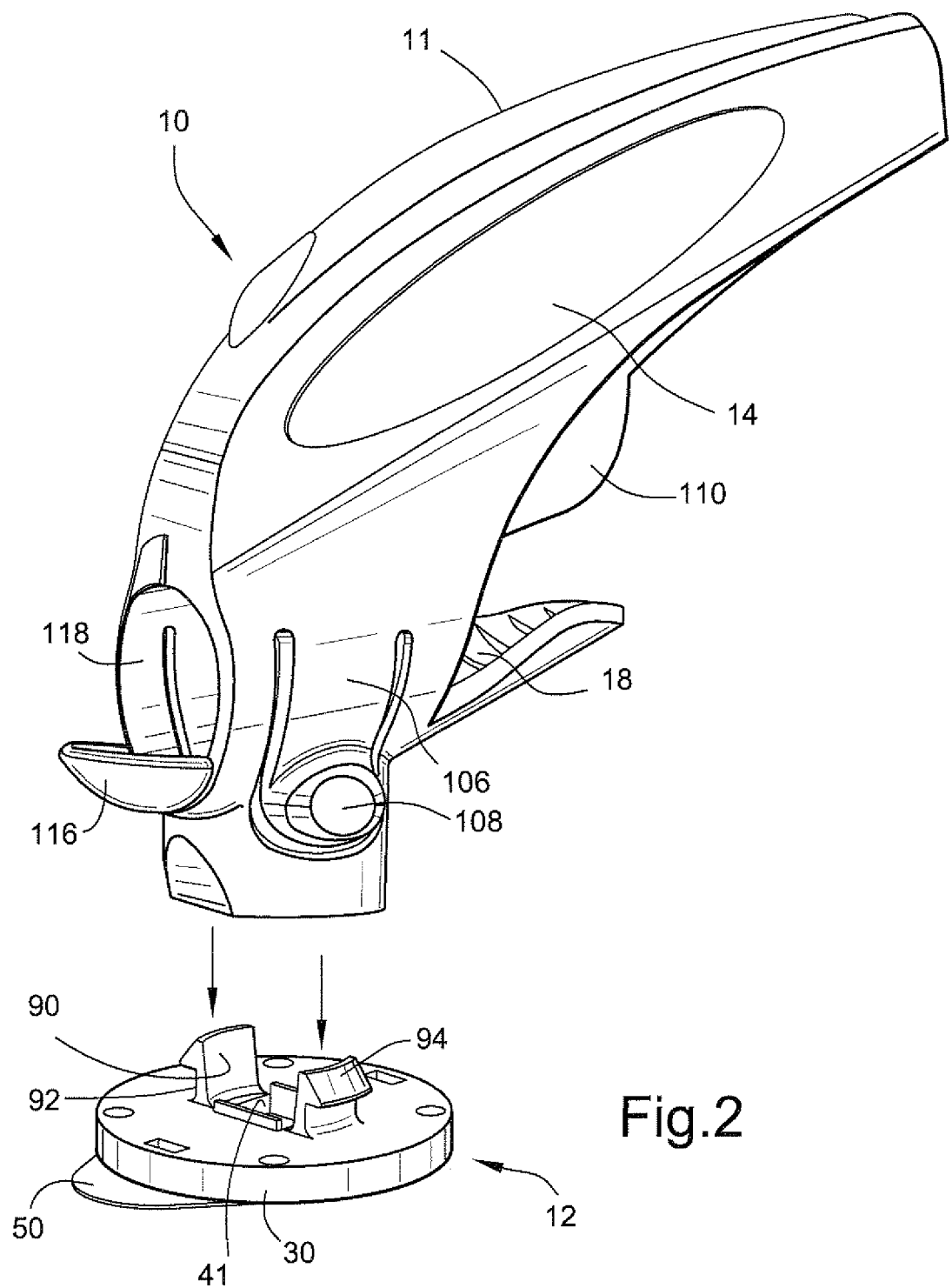
FIG. 2 is a perspective view similar of the first embodiment of the electrokinetic delivery device wherein the cartridge is released from the device.

FIGS. 1 to 4 show a portable self-contained light weight compact finger mounted electrokinetic medicament delivery device 10 and a cartridge 12 releasably attached to the delivery device 10. The device 10 includes a housing 14 mountable on and, in part, about an individual's finger or digit. The interior of the housing 14 may contain a self-contained power source 16, e.g., a battery, a counter electrode 18 electrically connected to the power source and forming part of a flex electrical circuit 20 carried by the housing 14. The device may be hand-held such as by securing the housing 14 to a finger of the hand. For example, an index finger is inserted through an aperture 118 of the device.

After the lid 50 is removed and the cartridge head applied to the target site on the skin, an electrical current is applied by the device to the medicament and to a counter electrode 18 in contact with the index finger. Alternatively, a trigger 11 may be used to actuate the application of electrical current.

Figure 4A:
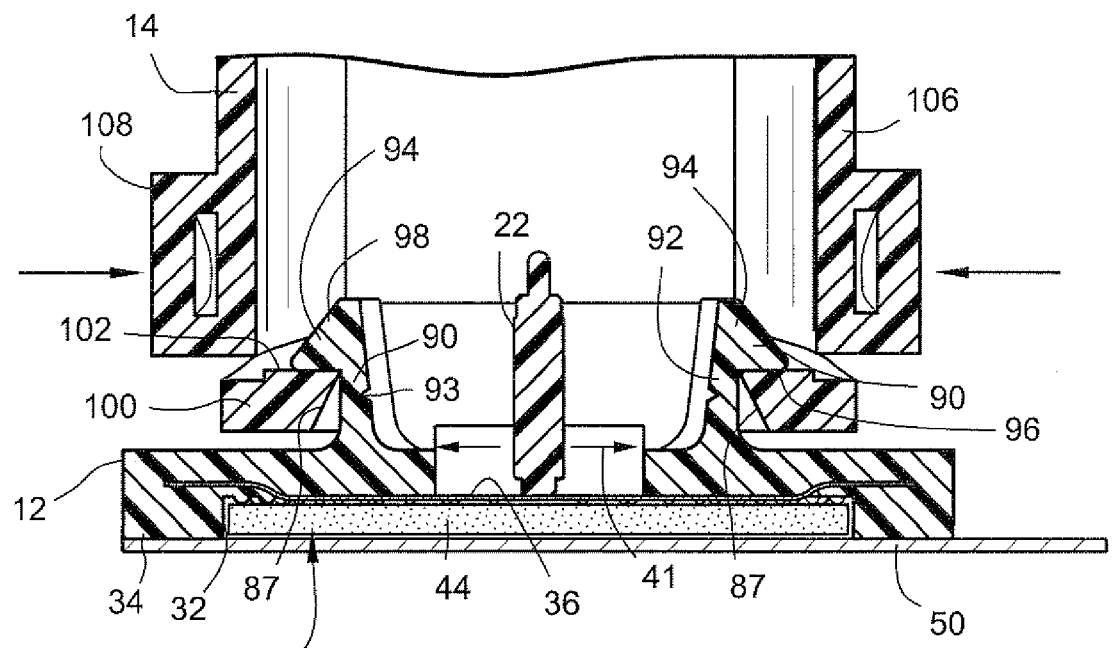
FIGS. 4A, 4B and 4C are fragmentary cross-sectional views of the device illustrating a sequence of steps to release the cartridge from the device.
Figure 5:
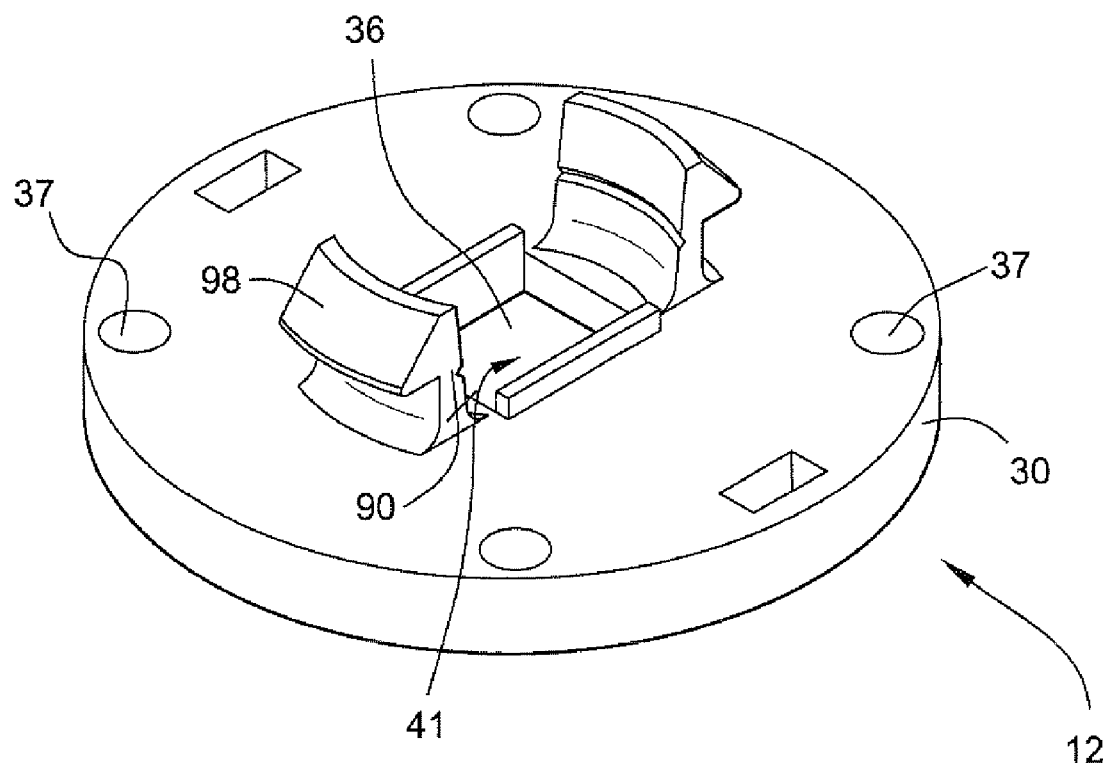
FIG. 5 is a perspective view of a cartridge, illustrating the backside of the cartridge which faces the device when the cartridge is coupled to the device.

Electrical current is provided to the medicament via an active electrode 36 (FIGS. 4A and 5). The flex circuit 20 provides an electrical path between the power source and active electrode. Electrical current flows through the active and counter electrodes, the medicament matrix, skin contact area, the individual and to the device. The current flow causes the medicament to penetrate the skin at the skin contact site where the cartridge is pressed against the skin. After the medicament is delivered, the cartridge 30 is released and removed from the housing by pressing the eject buttons 108 on opposite sides of the housing. The inward deflection of the buttons releases the posts 90 on a rear surface (e.g., second face) of the cartridge, and may forcibly eject the cartridge.

The cartridge 12 is preferably releasably secured to the device 10 at the distal end of the device housing 14. The releasable securement enables the device 10 to be re-used with additional cartridges. The individual cartridge 12 is intended for one-time usage.

To facilitate the electrical connection between the human individual's finger and the counter or tactile electrode 18, the electrode 18 is shaped, e.g., concave surface, to receive the undersurface of the individual's finger. To press the finger against the counter electrode 18, a living spring 110 exposed through the underside of the housing 14 biases the finger towards the counter electrode. Additionally, a finger stop 116 is provided to receive the tip of the individual's finger when engaged through the aperture 118 of the device to prevent excessive movement of the finger in the device.

The flex circuit 20 includes an arcuate portion 120 which extends along an inside surface of the housing 14. The arcuate shape ensures that the flex circuit is out of the way of the finger when in the aperture 118. The arcuate portion of the flex circuit provides an electrical connection between the circuit 20 and the counter electrode 18 that engages the finger. To further facilitate the electrical connection between the finger and the counter electrode 18, a moistened one-time use conductivity enhancing substrate 122 formed of a woven or non-woven material, e.g., a sponge, may be provided to wet the contact surfaces between the finger and counter electrode. The conductivity enhancing substrate 122 may be applied to an individual's finger prior to the insertion of the finger into the device. The conductivity enhancing substrate 122 may be impregnated with a hydrogel or other electrically conductive material, facilitating electrical connection between the individual's finger and the counter electrode 18 when the conductivity enhancing substrate 122 registers and contacts the counter electrode.

The flex circuit also includes a contact pin 22 effecting electrical connection with an active electrode 36 (FIG. 5) carried by the cartridge 12. The pin 22 makes electrical contact with the active electrode 36 for electrokinetic transport of the medicament carried by the cartridge 12 to the skin treatment site upon completion of an electrical circuit from the power source 16, through the flex circuit 20, pin 22, active electrode 36, medicament or hydration material carrying the medicament, the individual's body and a counter electrode or tactile electrode 18 carried by the housing 14 in electrical contact with power source 16. The flex circuit 20 may include a metallic strip spring 306 between the counter electrode 18 and the pin 22 to provide an electrical contact between the two.

Figure 3:
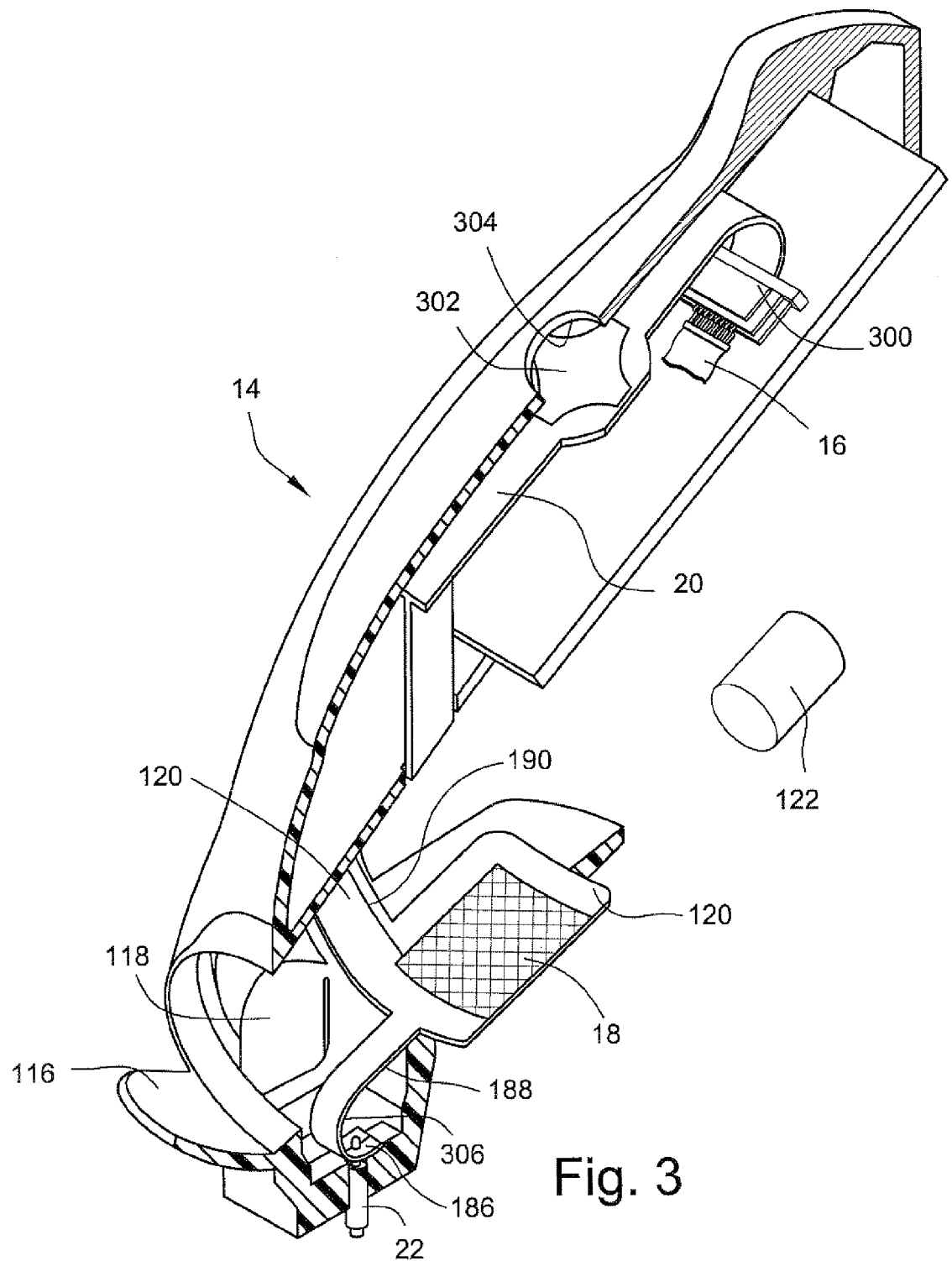
FIG. 3 is a perspective view of the device of FIG. 1 that shows the device in cross-section along a longitudinal cut to illustrate internal components of the device.

As best shown in FIG. 3, the flex circuit 20 is disposed within the housing 14. The flex circuit 20 includes a printed circuit board (PCB) board 300, an on-off switch 302 accessible through an opening 304 in the housing 14 and activated by a trigger (FIG. 1), the arcuate portion 120, the counter electrode 18 and the pin 22 for electrically coupling the flex circuit 20 and the active electrode 36 of the cartridge 12 when the cartridge is applied to the device 10. An electrical circuit is completed when the cartridge 12 is secured to device 10 to electrokinetically drive the medicament or the medicament and carrier therefor through the individual's skin to the treatment site. The electrical circuit includes the power source 16, the PCB 300, the on-off switch 302 (trigger 11) when placed in an on condition, the arcuate portion 120, the counter electrode 18, the pin 22, the active electrode 36, the medicament or the medicament and carrier therefor carried by the cartridge 12, the individual's body between the treatment site and the individual's finger electrically coupled to the counter or tactile electrode 18. Electric contact between the pin 22 and the PCB is provided by a conductive path 186 on a first side of a spring portion 188 of the flex circuit and the path 186 extends on a backside of the arcuate portion 120 of the flex circuit to the PCB. The finder side (opposite to the backside) of the arcuate portion includes the counter electrode 18 that is connected by a conductive path 190 on the flex circuit that extends to the PCB.

Figure 4B:
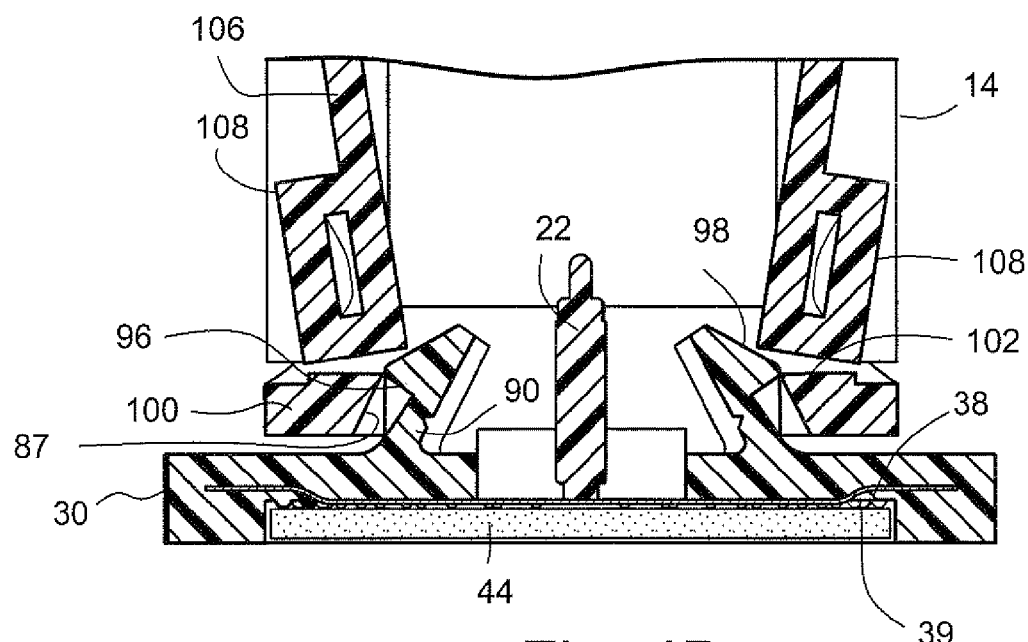
Figure 4C:
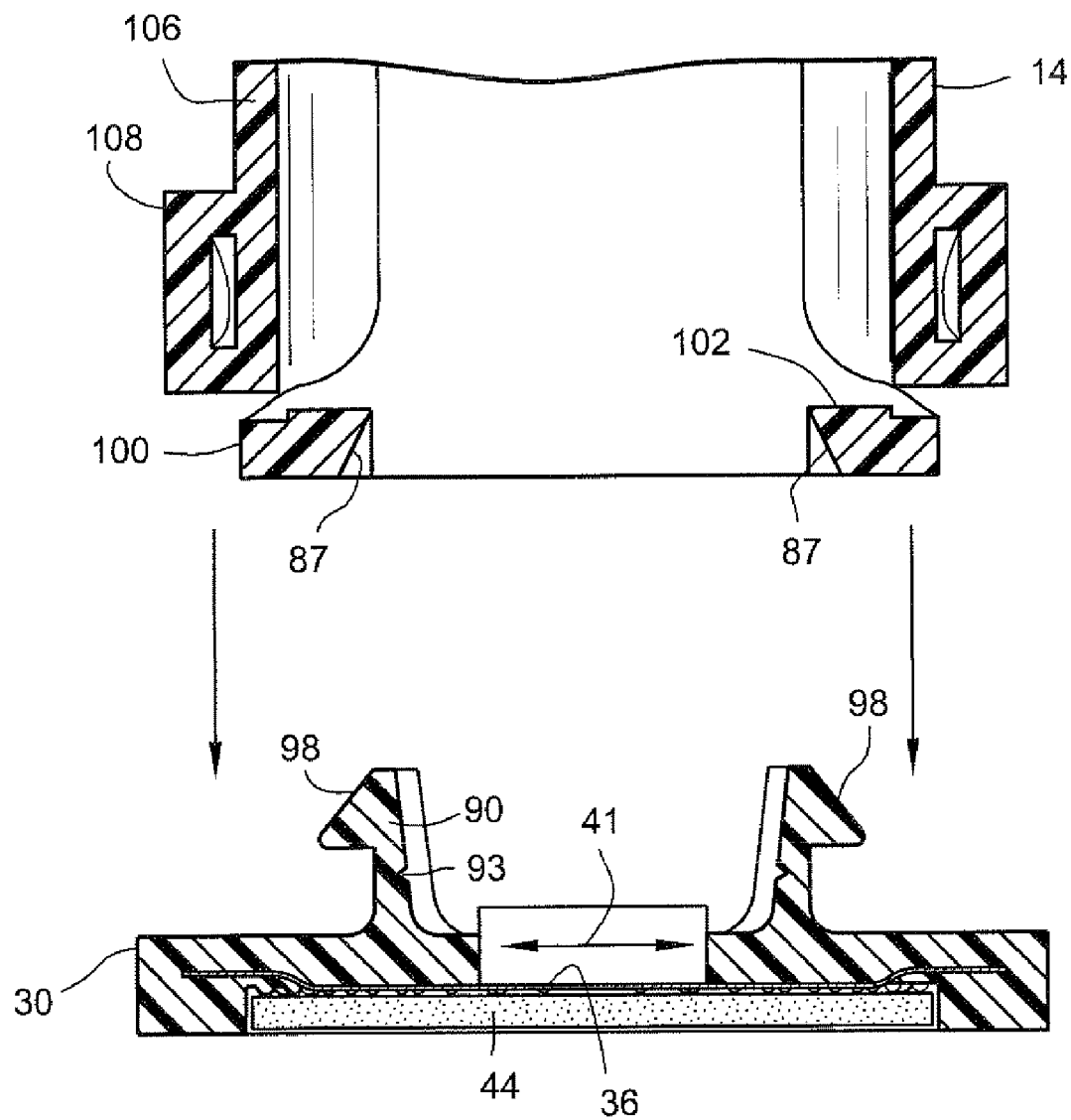

FIGS. 4A to 4C show the releasable connection between the cartridge 12 and the housing 14. The cartridge 12 is releasably secured to the housing 14 by a locking element which readily receives a cartridge 12 at the distal end of the housing, and secures the cartridge 12 to the cartridge applicator device 10 in a manner ensuring electrical contact between the flex circuit 20 and the active electrode 36. Generally, a locking element includes a cartridge component, e.g., latch posts 90, and a housing component, e.g. ledges 100, that releasably engages the cartridge component. The locking element enables the cartridge 12 to be released, preferably forcibly ejected, from the housing subsequent to use of the cartridge.

In particular, the locking element includes a pair of resiliently flexible posts 90 which preferably flank or straddle an opening 41 extending from the rear surface (face) of the front surface. The opening exposes the active electrode 36 seated in a recess 32 in the front surface of the cartridge head 30. The front surface further includes an annular rim 34 that supports a lid 50 that can be removed to exposes a matrix 44. The lid 50 is shown on the front surface of the cartridge in FIG. 4A. The lid is removed before the cartridge is applied to skin and the application of medicament. The lid is shown removed and the cartridge is in the process of being ejected in FIGS. 4B and 4C, signifying that the cartridge has been used and is being discarded.

Each post 90 includes a neck 92 which terminates at its distal end in an outwardly directed flange 94 and, at its proximate end, is integral with the cartridge head 30. Flange 94 has an undersurface or flat surface 96 which extends laterally and generally parallel to a plane of the head 30. Each flange 94 also includes a tapered outer surface 98 providing a sloped distal end of post 90 preferably along the full lateral extent of the flange 94.

The distal end of the housing 14 (which receives the cartridge) includes a pair of oppositely disposed ledges 100 of partial annular rims. The ledges have flats 102 along upper surfaces thereof parallel to the flats 96 along the underside of the flanges 94. The flats 102 of the housing ledges 100 engage the flats 96 of the cartridge posts 90 to latch the cartridge in the housing. The housing ledges 100 may have adjacent tapered surfaces 87 along interior surfaces of the housing to facilitate the sliding of the cartridge into the device and the ejection of the cartridge from the device.

Because of the resilient flexible nature of the posts 90, the posts deflect inwardly toward one another as the cartridge 12 is displaced toward and into the distal end of the housing 14. The inward deflection is caused by the insertion of the cartridge that engages the tapered surfaces 98 of posts 90 along the tapered surfaces 87 of the inner edges of the ledges 100. Once the flanges 94 extend past the ledges 100, the posts resiliently flex outwardly away from one another under their natural bias such that the undersides 96 of the posts engage and bear against the flats 102 of the ledges 100.

The pin 22 of the housing makes electrical connection with the active electrode 36 in the cartridge, upon securement of the cartridge 12 to the device 10 by engaging the active electrode 36 through the opening 41 of the cartridge 12. The resilient nature of the flex circuit, e.g., a metallic spring 306, biases the pin 22 into electrical contact with the active electrode 36. The bias of the flex circuit also pushes surface 96 and flats 102 in contact with one another.

To release and preferably eject the cartridge 12 from the housing 14, the distal end of the housing 14 includes a pair of eject buttons 108 on cantilevered springs 106 which are arms formed integrally with the housing. Springs 106 terminate at their free ends in push ejection buttons 108 along opposite sides of housing 14. The springs 106 have outer surfaces contoured similarly as adjacent portions of the housing 14. The push buttons 108 may be pressed inwardly toward one another against the bias of the springs 106. As best illustrated in FIG. 4B, inward deflection of the push buttons 108 causes inner edges of the springs 106 to engage the outer tapered surfaces 98 of the flanges 94 of posts 90. Further displacement of the push buttons 108 toward one another moves the flanges 94 of the posts toward one another and off the flats 102 of the cartridge ledges 100. When the flats 96 of the flanges 94 of the posts clear the flats 102 of the housing, the cartridge 12 is released from the device 10.

The cooperation of the flanges 94 and the tapered inside surfaces 87 of the ledges 100 enable the cartridge 12 to be ejected from the device 10 with a positive forceful movement of the cartridge away from the device. The return bias of the posts (to return to their unbiased positions compare FIGS. 4B and 4C) causes the tips of the flanges 94 to bear against the tapered surfaces 87 of the ledges 100, and impart a force on the cartridge 12 to forcibly eject the cartridge from the device. Tapered surfaces 87 on the housing ledges 100 facilitates insertion and ejection of the cartridge in and out of the housing.

The posts 90 can be configured to prevent reapplication of the cartridge to the device after a one time usage. For example, the posts 90 may have weakened portions 93 along their necks 92 enabling the posts to collapse or break off during the ejection process thereby disabling the cartridge from subsequent reattachment to the device 10. The weakened portions should be strong to allow the cartridge to be inserted and held in the housing.

The front surface of the head 30 includes a recess 32 defined by an annular rim 34 about the head 30. An active electrode 36 is disposed within the recess 32. The active electrode has a broad surface area exposed towards the front surface of the head 30 within a peripheral margin or boundary 38 between the outer edge of the electrode 36 and the rim 34 of the head 30. The surface area of the active electrode 36 on the front side of the head 30 is generally co-extensive with the recess 32 except for the margin 38. In the illustrated cartridge, the head 30, the exposed portion of the active electrode 36 and the margin 38 are circular. Other configurations, e.g., rectangular, oval and triangular, may be utilized for the geometry of the cartridge and for the matrix and active electrode. The recessed annular margin 38 in the recess 32 of the head 30 includes a plurality of raised dimples 39, e.g., raised projections from the surface of the margin 38, at circumferentially spaced locations about the margin 38. The dimples may be radially and circumferentially spaced one from the other. Except for the active electrode 36, medicament matrix membrane 44 and lid 50, the head 30 may be formed of a polymer material.

FIG. 5 is an enlarged view of the read surface of the cartridge 12. The cartridge 12 generally includes a head 30, e.g., a disc, having on its back or rear side a portion of an locking element, e.g., posts 90, for releasably securing the cartridge 12 to the housing. To provide an electrical connection between the active electrode 36 of the cartridge 12 and the flex circuit 20, the rear surface of the head 30 has an opening 41, preferably aligned with a central portion of the head 30, through which the back of the active electrode 36 is exposed. The pin 22 in electrical connection with the flex circuit 20 extends through the opening 41 to make electrical connection with the backside portion of the electrode 36 when the cartridge 12 is secured to the housing. The back of cartridge 12 includes one or more openings 37 which expose a portion of electrode 36. The additional exposure of the electrode through openings 37 provides a secondary electrical access to the active electrode such as to facilitate diagnostic testing during manufacture and can provide an alternate access for the pin 22.

Figure 6:
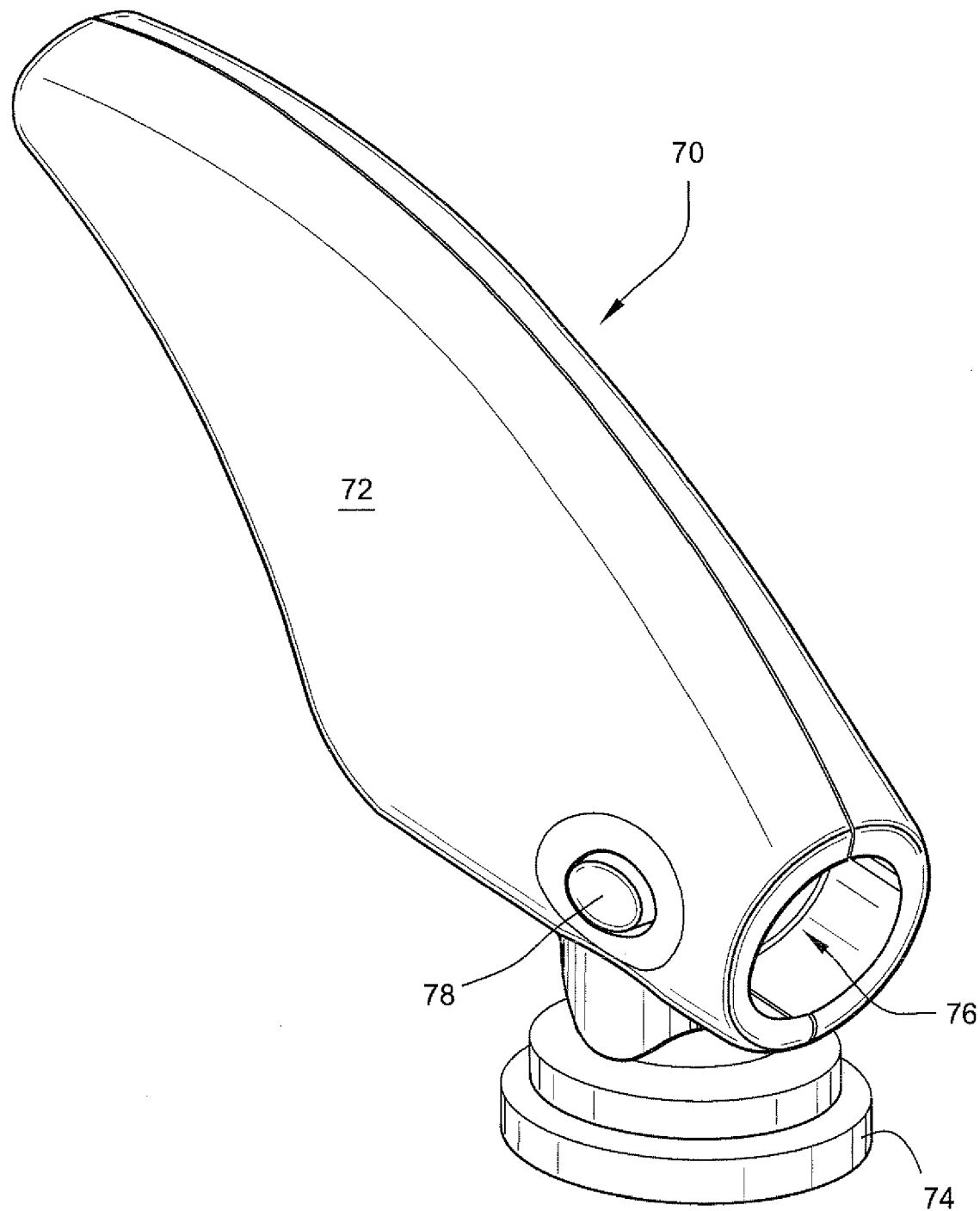
FIG. 6 is a perspective side and front view of a second embodiment of the electrokinetic delivery device.
Figure 7:
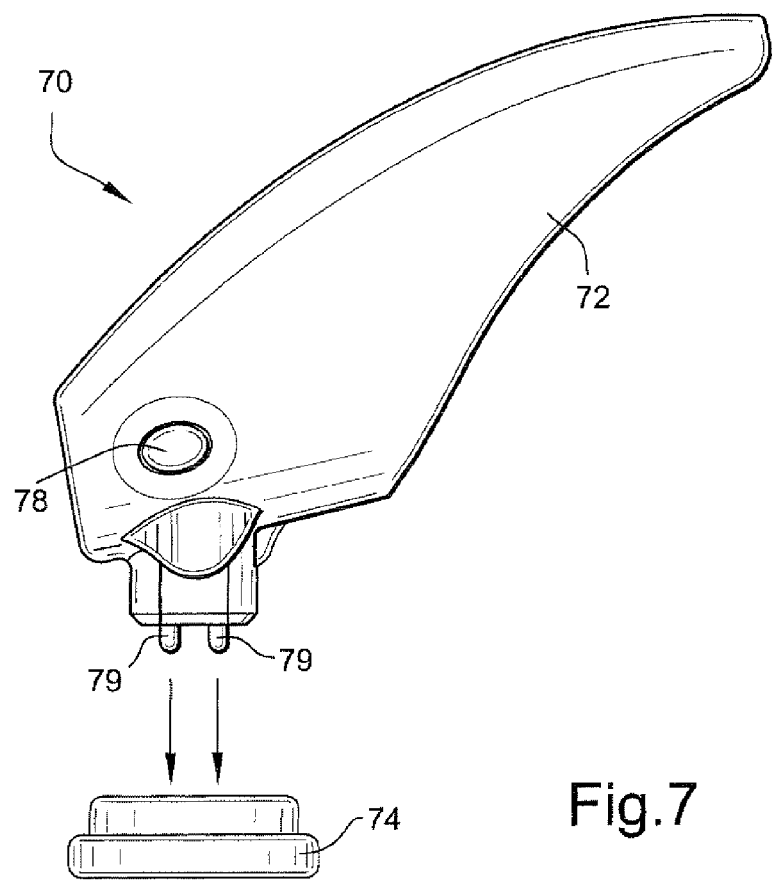
FIGS. 7 and 8 are side views of a second embodiment of the device showing the cartridge attached and removed from the housing.
Figure 8:
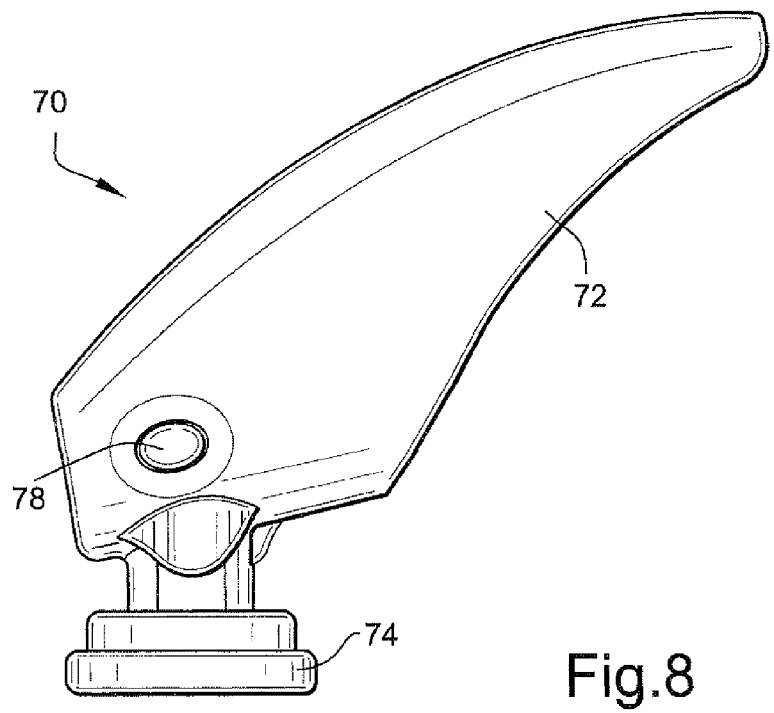

FIG. 6 is a perspective view of an alternative device 70 having a housing 72, cartridge 74, finger aperture 76 and eject buttons 78. The alternate device 70 includes many of the same components of the device 10 described above. The alternative device 70 is sleek, comfortable to hold and intuitive to operate. FIGS. 7 and 8 are side views of the alternative device 70 in which the cartridge is ejected (FIG. 7) and attached (FIG. 8). Further, the alternative device may include a plurality of metallic pins 79 to provide electrical connection between the electronics and power source in the housing and the active electrode in the cartridge.

Figure 9:
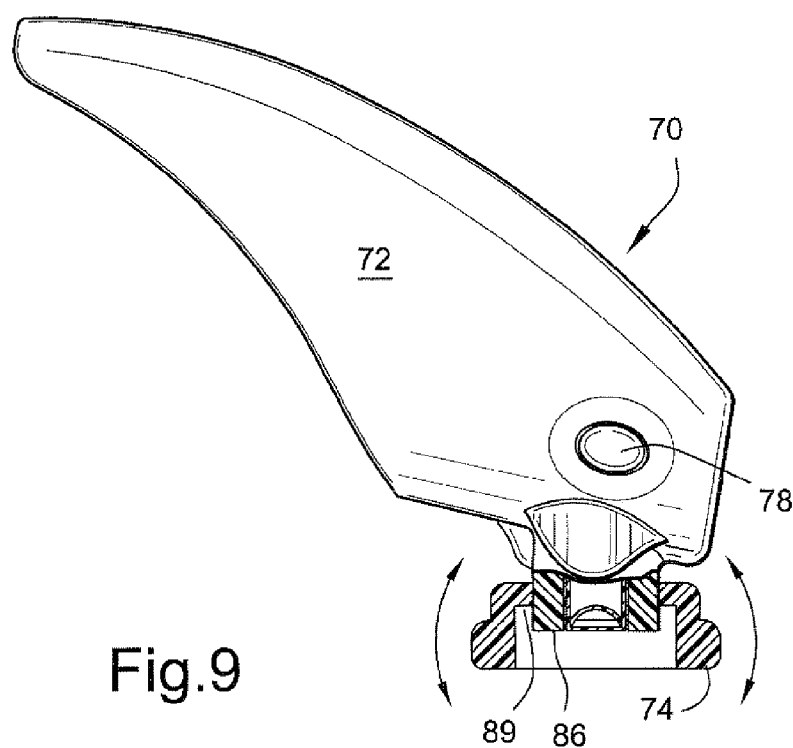
FIG. 9 is a side view of the second embodiment of the device showing in cross section the cartridge and the attachment for the cartridge.
Figure 10:
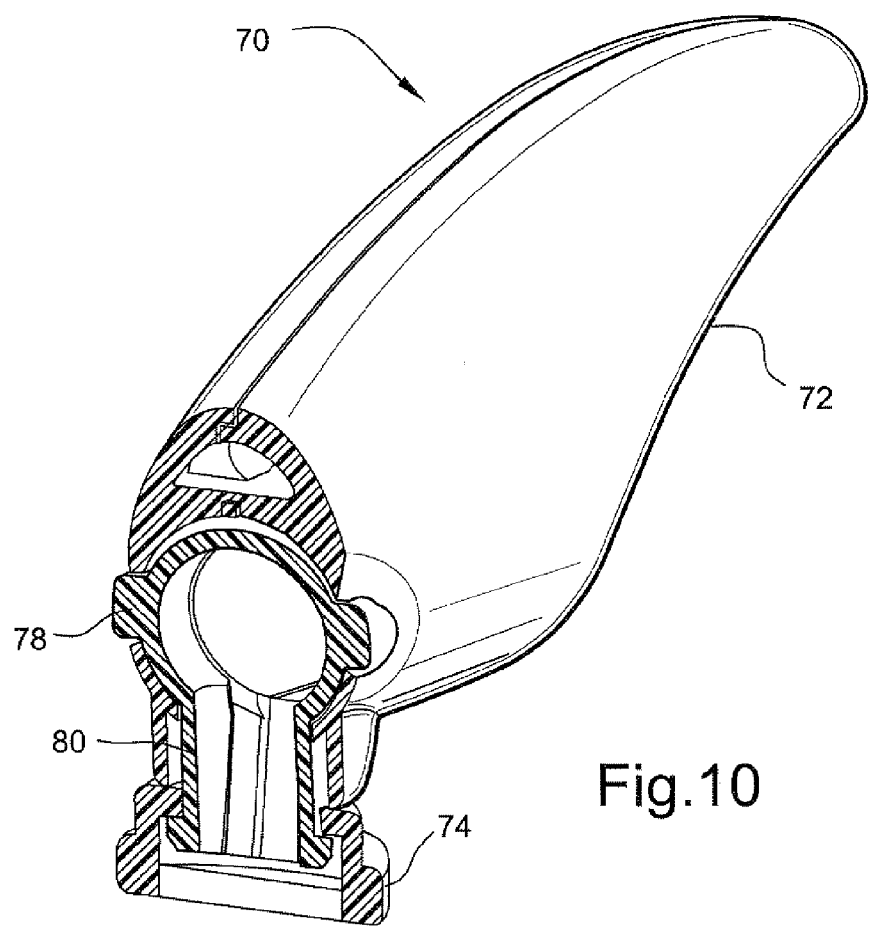
FIG. 10 is a perspective view of the second embodiment of the device showing the front portion of the device in cross section.
Figure 11:
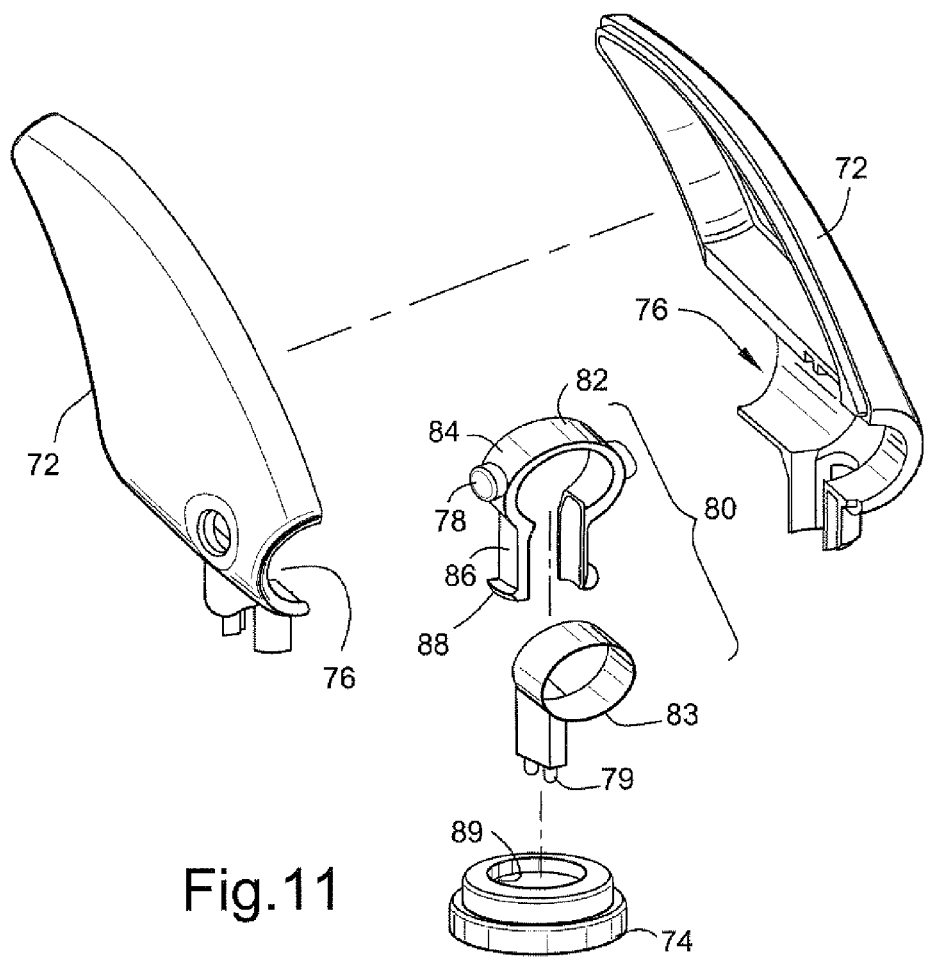
FIG. 11 is an exploded view of the second embodiment of the device.

FIGS. 9 to 11 show an locking element 80 for releasably connecting the cartridge 74 to the housing 72 in the alternative device 70. The mechanism 80 allows for a slight pivoting, e.g., a range of angular movement of 5 to 10 degrees, about the axis of the cartridge. The pivoting cartridge ensures that the removal of the foil lid 50 (see FIG. 4A) will not inadvertently release the cartridge. The locking element 80 comprises a spring clip 82 and a contact ring 83 with the electrical contact pins 79, and an inner latch ledge 89 in the cartridge. The spring clip is generally key hole shaped in front plan view having a bulbous section 84 that forms a spring to separate a pair of arms 86 that include ledges 88 to latch the inner annular ledge 89 of the cartridge. The spring clip may be a resilient plastic or metallic strip material. The outermost surfaces of the bulbous section include the eject buttons 78. The spring clip fits within the distal end of the housing 72 that includes inner recesses and grooves to receive the spring clip. Apertures on opposite sides of the housing allow the eject buttons 78 to protrude through the housing. When the buttons are pressed together, the arms deflect inward and release the cartridge. The contact ring 83 fits within the bulbous section and provides an electrical contact between the power supply and electronics (not shown) and pins 79. The contact ring 83 may be a conductive material, e.g., a thin metal material. The pins 79 provide an electrical contact between the active electrode and flex circuit.

Figure 12:
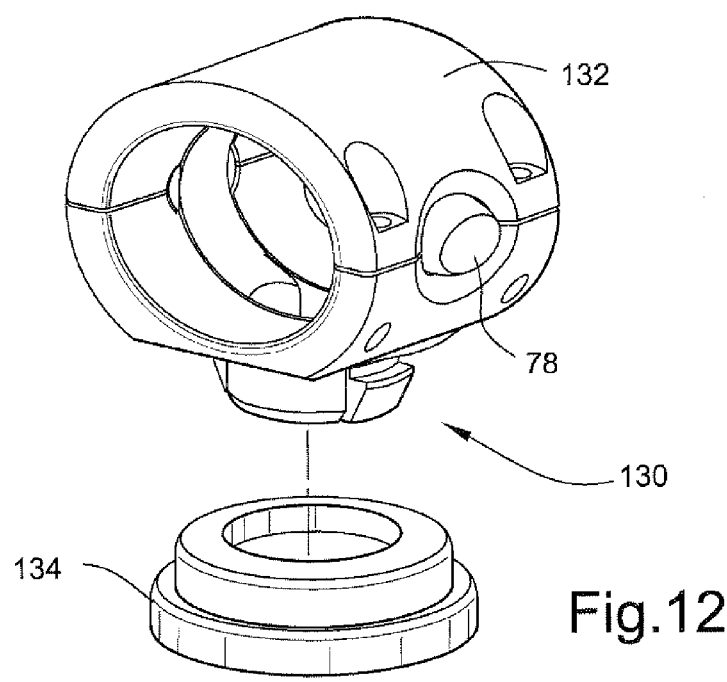
FIGS. 12 to 14 are front perspective views and cross-sectional views of an locking element for a third embodiment of the device, where the locking element couples a cartridge to a housing of the device.
Figure 13:
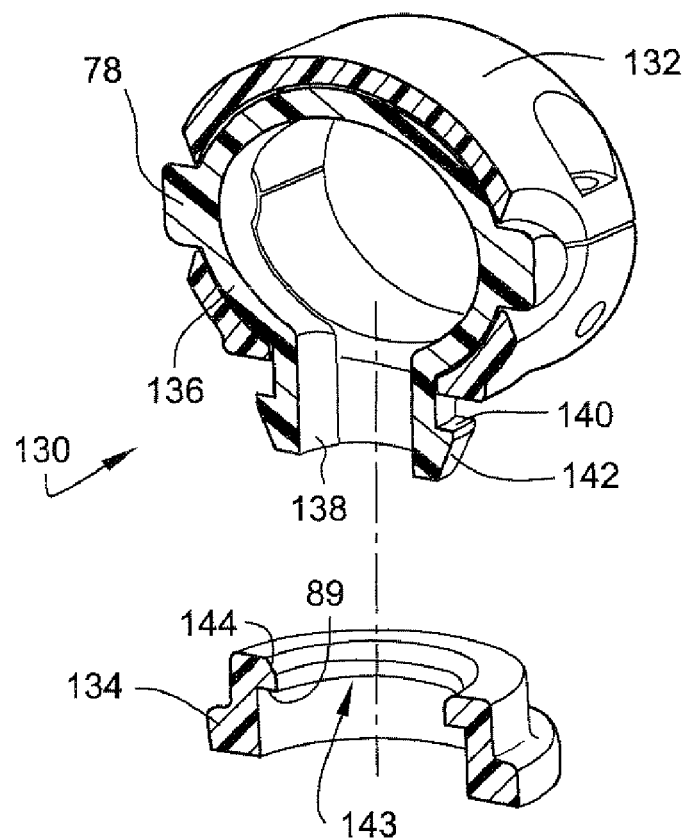
Figure 14:
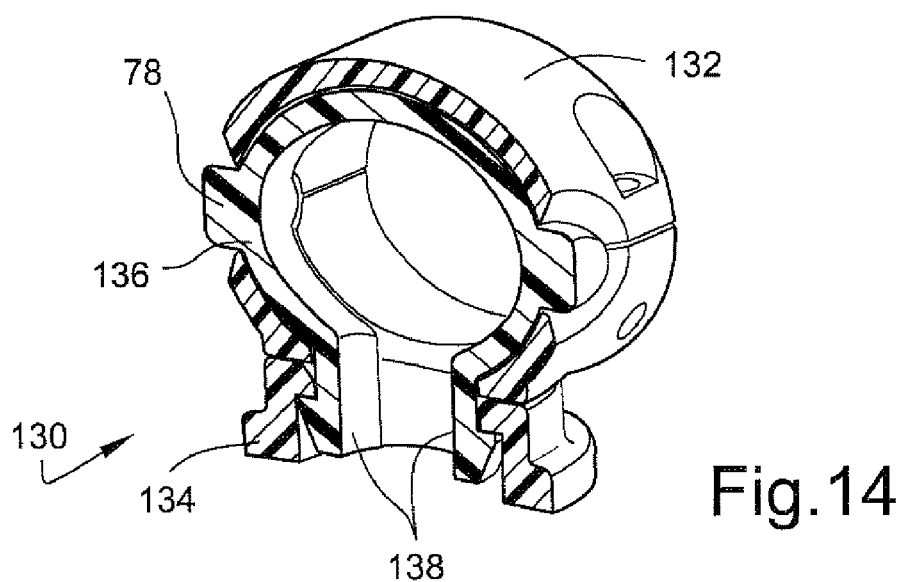

FIGS. 12, 13 and 14 illustrate another locking element 130 in a housing having a relatively thin finger section 132 with a finger aperture. The cartridge 134 snaps onto latch arms 138 of the spring clip 136 in the finger section of the housing 132. The spring clip may be metallic or a resilient plastic strip material. The locking element 130 is similar to the locking element 80 shown in FIGS. 9 to 11 in that it includes a spring clip 136 and a contact ring and pins (not shown). The arms 138 of the spring clip 136 are short and include a ledge 140 and a tapered bevel 142 distal to the ledge. The aperture 143 in the rear of the cartridge 134 has a beveled rim 144 across which slides the beveled surface 142 of latch on the arms 138 as the cartridge is inserted into the mechanism 130. The sliding beveled surfaces deflect the arms 138 of the clip inward until the ledges 140 slide past the ledges 89 of the inner recess of the cartridge. When the ledges 89, 140 pass each other, the arms 138 snap into the cartridge and the ledges 89, 140 engage the cartridge to the housing, as shown in FIG. 14. An advantage of the spring clip mechanisms 82 (FIG. 11), 136 is that it allows for generous manufacturing tolerances of the mechanism and the cartridge.

Figure 15:
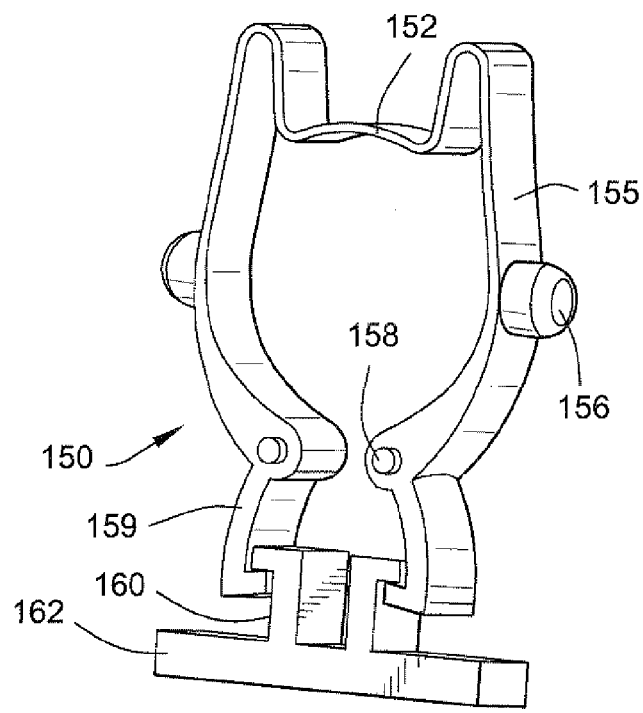
FIGS. 15 and 16 are a front view and a perspective view, respectively, of a spring clip for a cartridge locking element for a further embodiment of the device.
Figure 16:
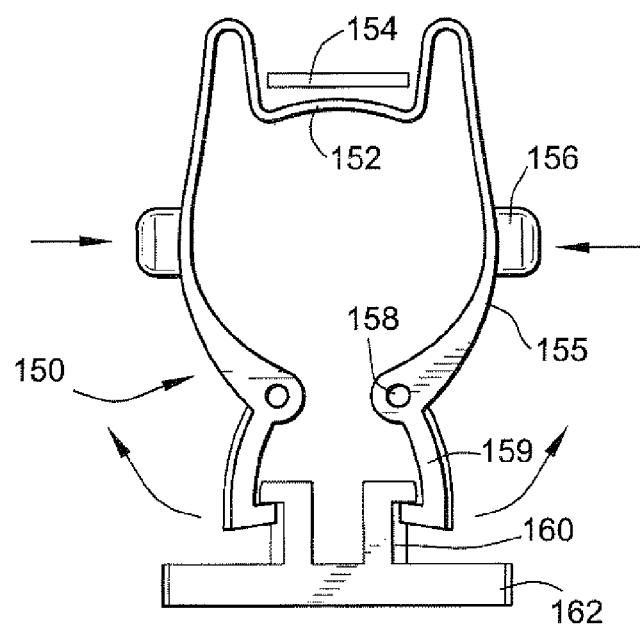

FIGS. 15 and 16 show another spring clip 150 having an upper cupped region 152 that allows for a printed circuit board 154, e.g., the flex circuit, to be mounted in the housing above the spring clip. The bulbous section 155 of the spring clip includes the eject buttons 156 that extend from the housing. The lower portion of the bulbous section includes pivot points 158 that attach to posts in the housing. When the ejection buttons are squeezed (as shown by inwardly pointing arrows), the clip pivots about the posts and the arms 159 swing outward (see outwardly pointing arrows) to release the posts 160 of the cartridge 162. The buttons are depressed to insert the cartridge in between the arms 159 and to release the cartridge.

Figure 17:
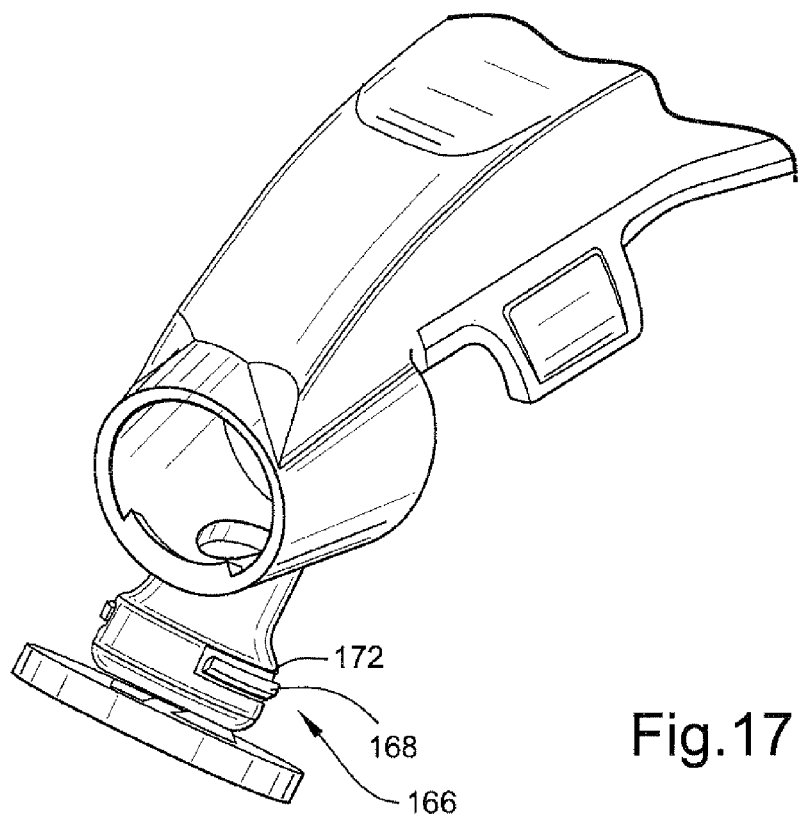
FIGS. 17 and 18 are a perspective view and a partial cross-sectional view, respectively, of another cartridge locking element for a fourth embodiment of the device.
Figure 18:
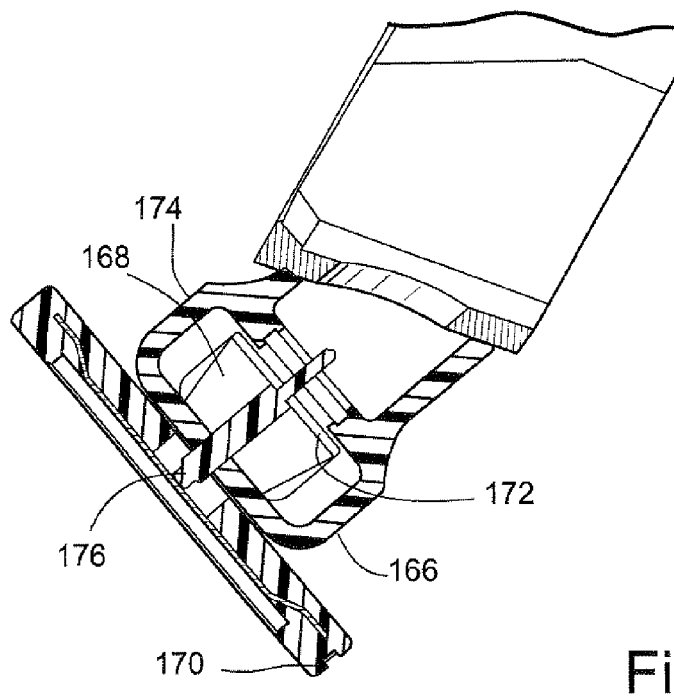

FIGS. 17 and 18 show a perspective view and a cross-sectional view of another locking element 166 in which the posts 168 of the cartridge 170 snap into slots 172 in a nose section 174 of the housing. The nose section 174 is hollow and has slots on opposite sides to receive the posts of the cartridge. The slots may extend through the walls of the nose section. The posts have a distal flange 172 and tapered forward surfaces. The posts deflect inwardly as their tapered surfaces slide into the nose section while the cartridge is inserted into the nose. Once in the nose, flanges on the lower surfaces of the flanges on posts snap into the slots. The flanges on the posts extend through the slots. To remove the cartridge, the flanges 172 on the post are pressed inward by pinching with the user's fingers to deflect the posts and allow the cartridge to slide out of the nose. The electrical contact pin 176 extends through a central region of the nose and provides a contact between the active electrode in the cartridge and the power supply in the housing.

Figure 19:
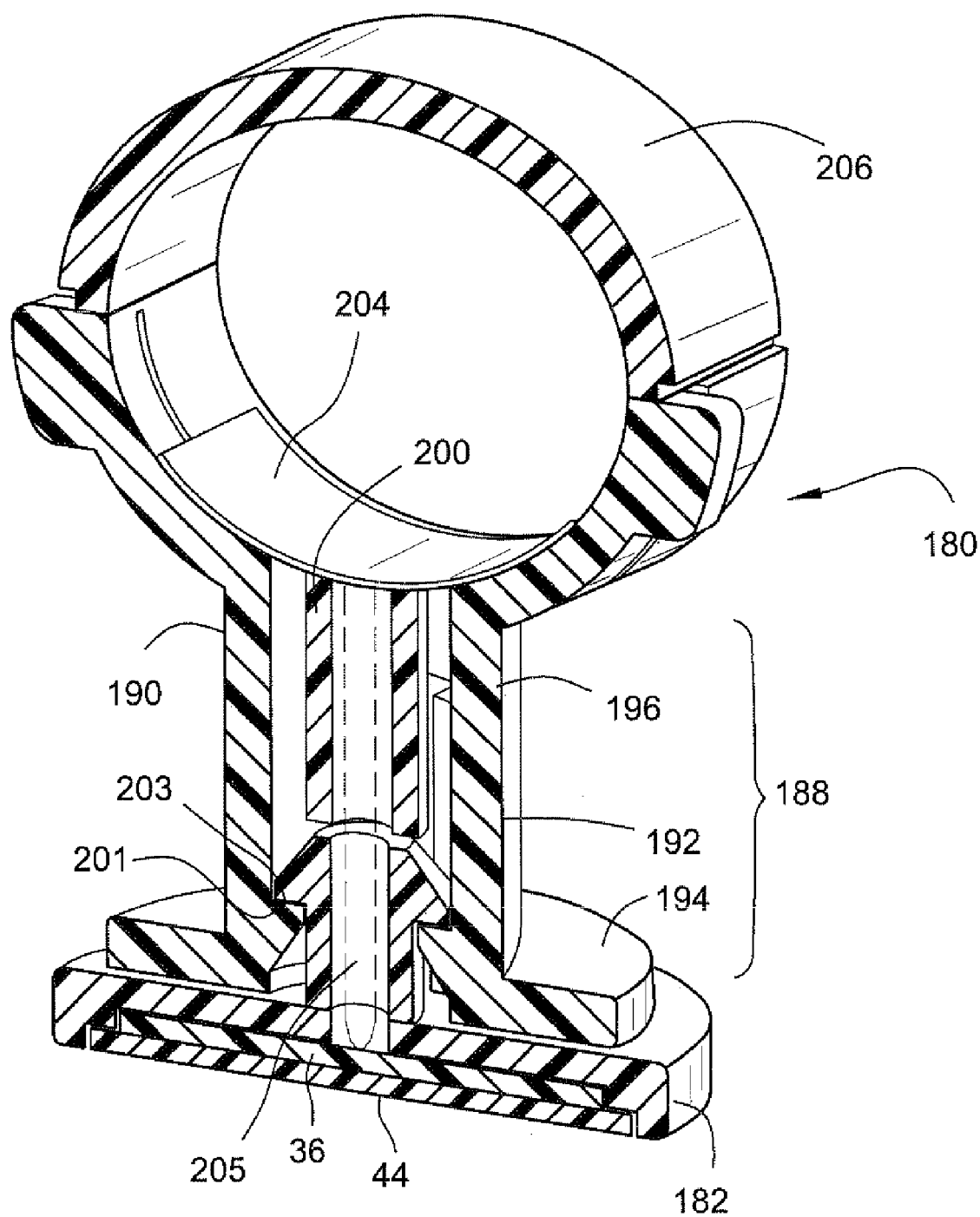
FIGS. 19 and 20 are a cross-sectional view and an exploded view, respectively, of an locking element and cartridge for a fifth embodiment of the device.
Figure 20:
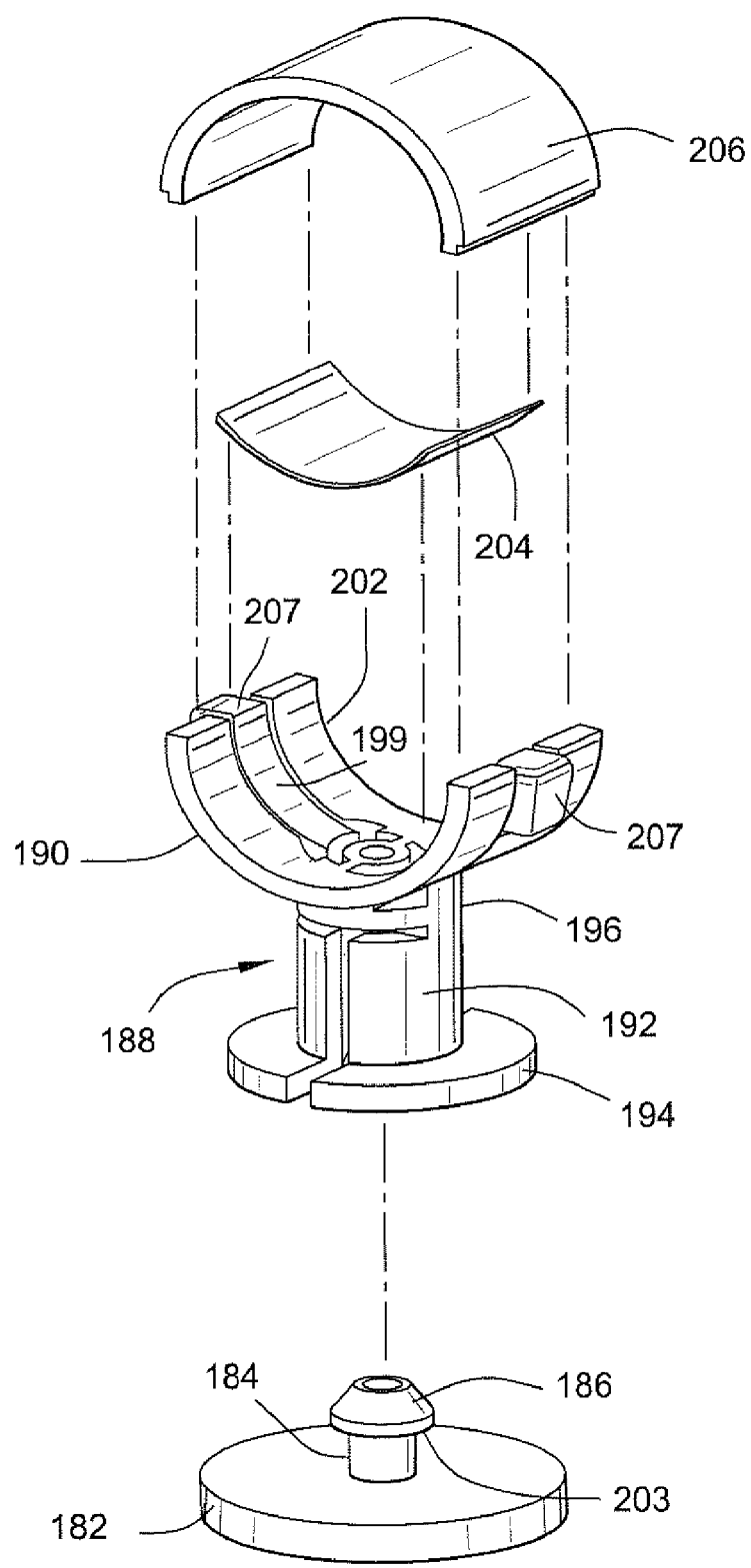
Figure 21:
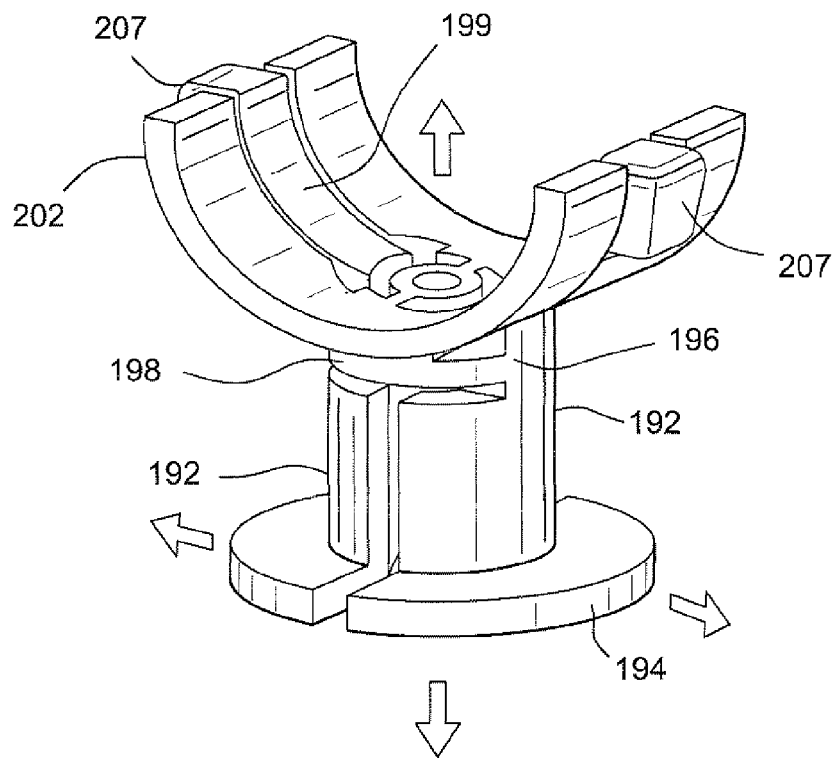
FIGS. 21 and 22 are a perspective view and cross-sectional view, respectively, of a lower body of the locking element shown in FIGS. 19 and 20.
Figure 22:
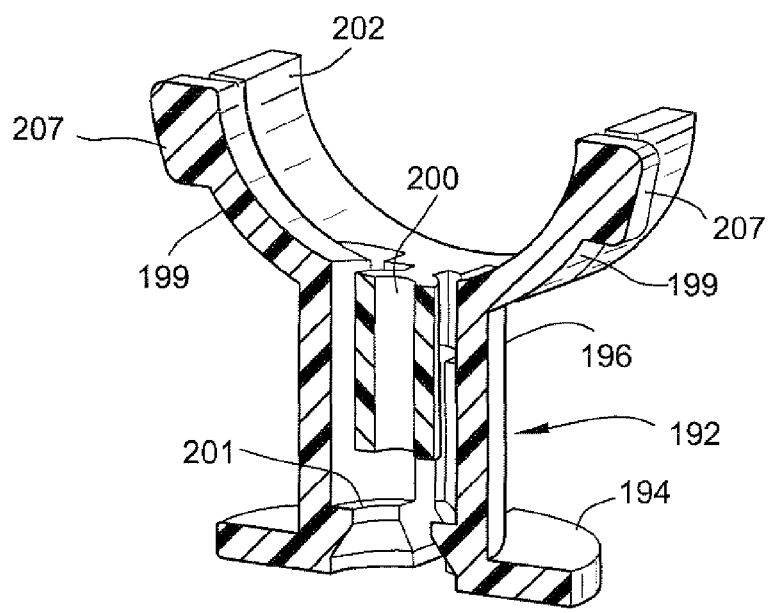

FIGS. 19 and 20 are a cross-sectional view and an exploded view of a fifth locking element 180 and cartridge 182. FIGS. 21 and 22 are a perspective view and cross-sectional view of a lower body 190 of the mechanism 180. The cartridge has a center post 184 with a frustoconical head 186 that is inserted in the hollow nose 188 of the locking element. A lower body 190 of the locking element includes the nose 188 which is formed by a pair of arms 192 that together form a generally cylindrical body of the nose and an annular flange 194 at the distal end of the nose. A pivot point 196 is at a mid-portion of the arms. The pivot point 196 may be part of an annular ring 198 (see FIG. 21) that extends entirely around the nose section. Alternatively, a pivot joint, e.g., slot in the ring section and rod in the arms, may be formed at the proximal end of the arms with the ring section of the nose. The arms 192 extend past the pivot point and form a lever arm 199 (FIG. 22) that has the buttons 207. As the buttons are squeezed together, the levers 199 cause the arms to pivot and force outward the flanges 194 (see opposite arrows in FIG. 21). Ledges 201 on inside surfaces of the flanges 194 latch the lower flats 203 of the head 186 of the post 184 on the cartridge. When the buttons are depressed, the outward movement of the arms 192 releases ledges 201 from the flat 203 of the post 184 to release the cartridge 182.

The lower body 190 may be formed as a single molded plastic part. The body 190 further includes a central pin shaft 200 (FIG. 22) to axially support a conductive pin 205 (FIG. 19) that engages the active electrode 36 and biases the electrode against the medicament matrix 44. Ribs between the shaft and the ring 198 support the shaft in the hollow nose of the lower body 190. The lever arm 199 may be curved and be in a gap between U-shaped supports 202 of the body 190. A metallic contact plate 204 is seated on an upper surface of the lever arms 199 and U-shaped supports 202 to provide an electrical contact between the pin 205 and power source. An inverted U-shaped upper body 206 caps the U-shaped supports 202 and together form a figure aperture.

Figure 23:
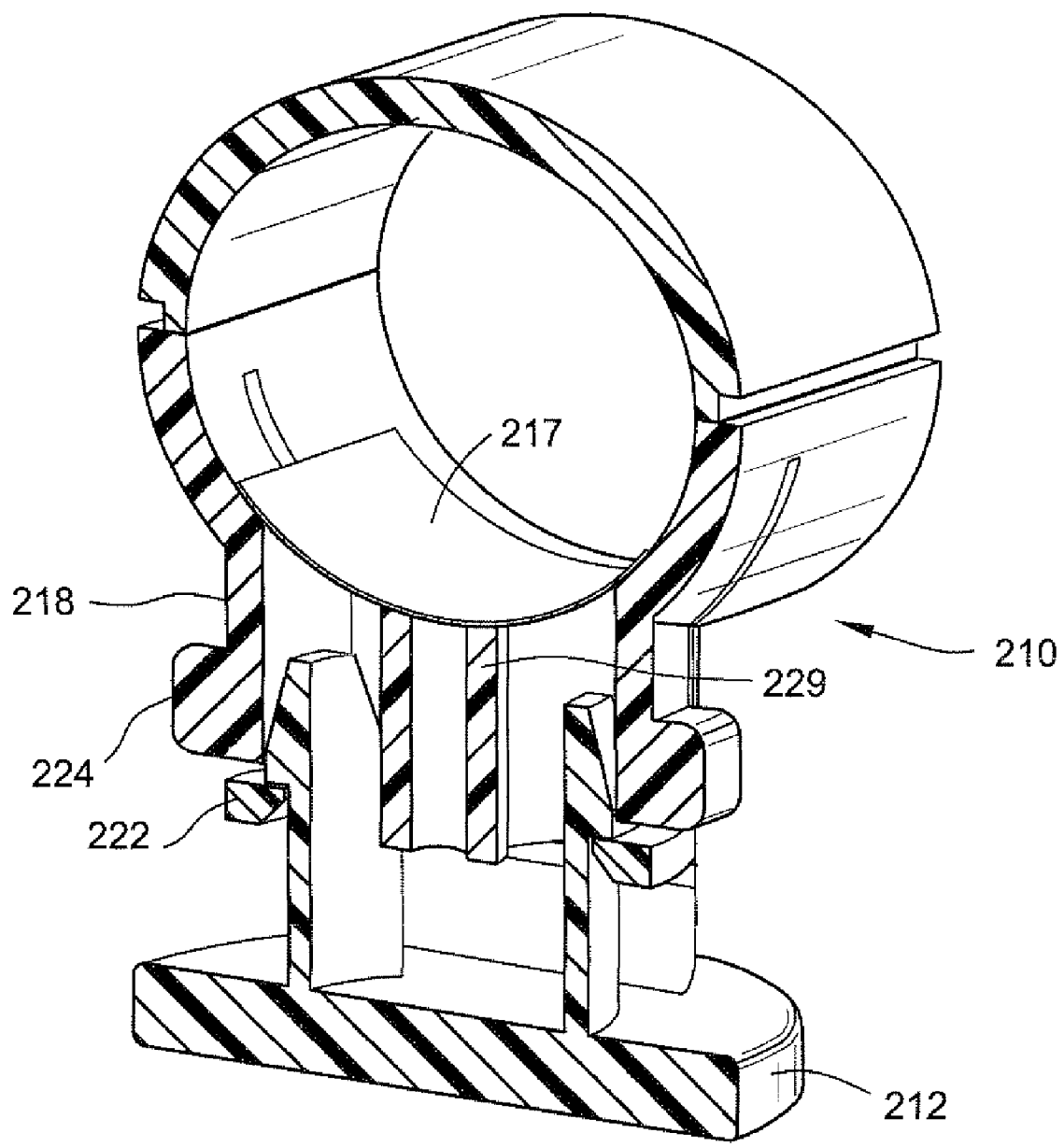
FIGS. 23 and 24 are a cross-sectional view and an exploded view, respectively, of a cartridge locking element and cartridge for a sixth embodiment of the device.
Figure 24:
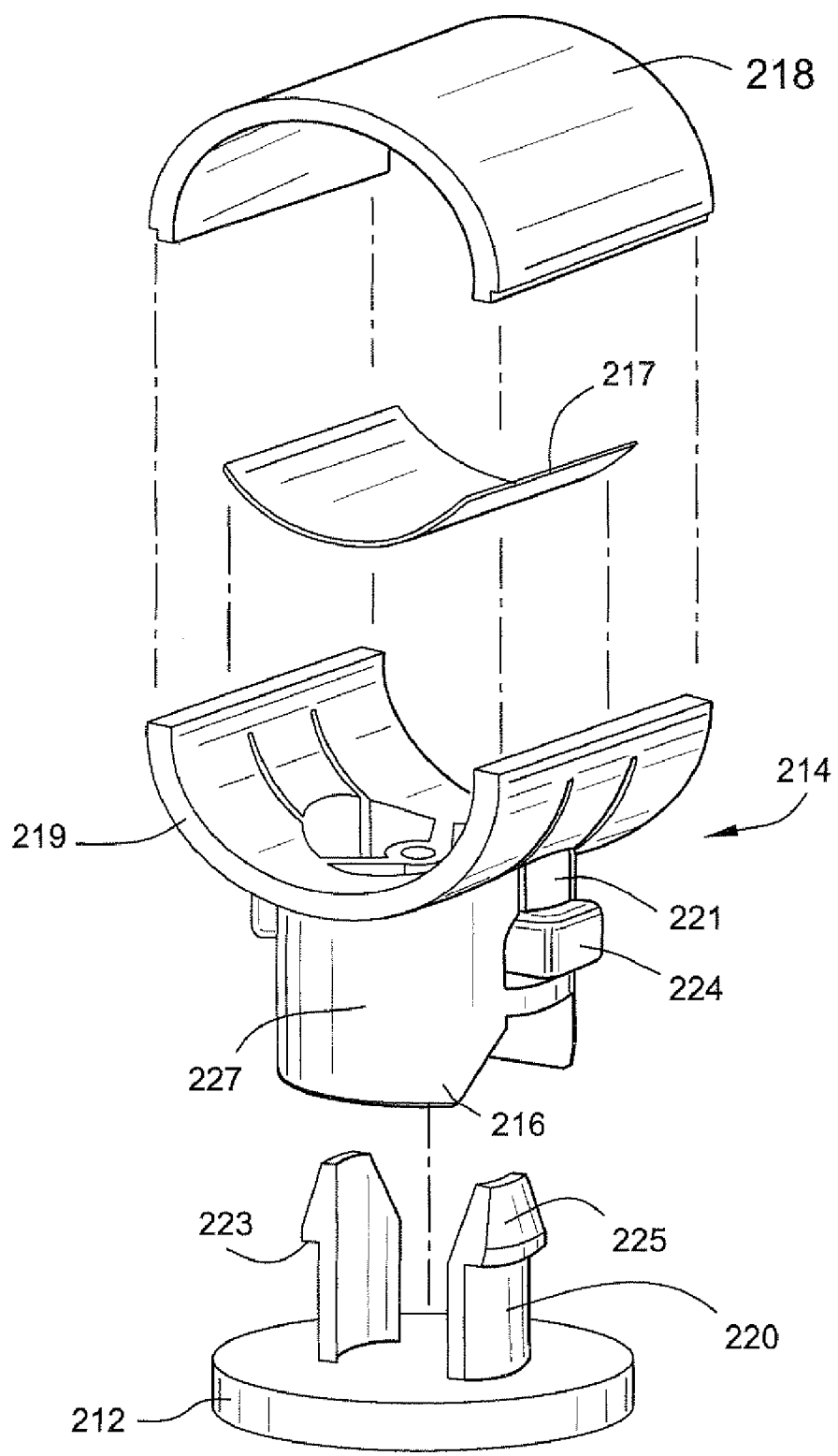
Figure 25:
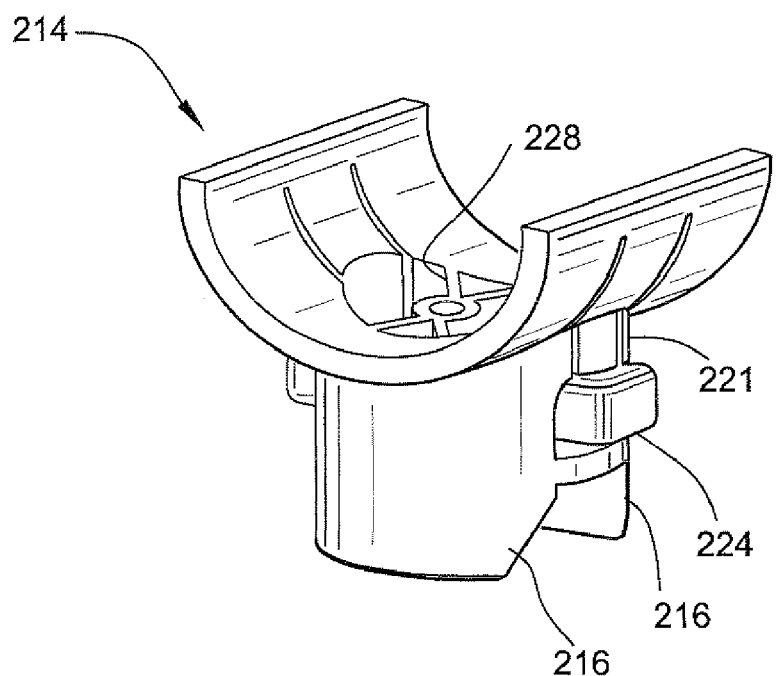
FIGS. 25 and 26 are a perspective view and cross-sectional view, respectively, of a lower body the cartridge locking element shown in FIGS. 23 and 24.
Figure 26:
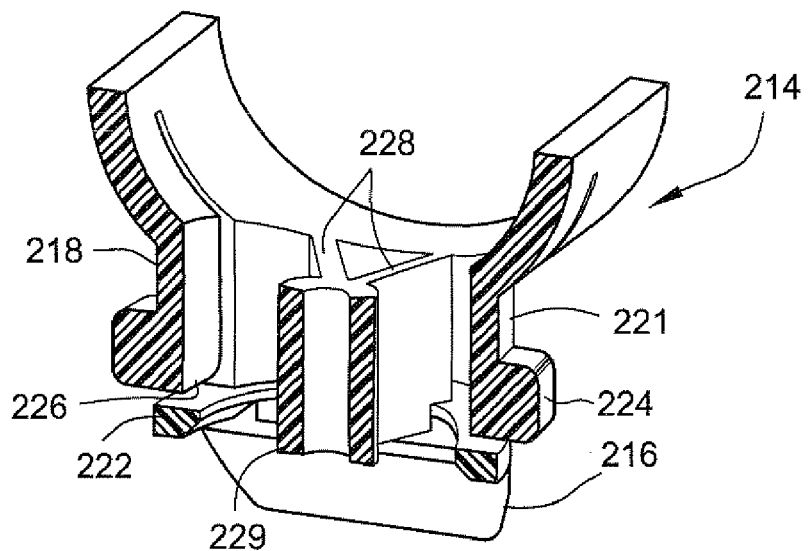

FIGS. 23 and 24 are a cross-sectional view and an exploded view, respectively, of another locking element 210 and cartridge 212, which includes an active electrode and medicament matrix which are not shown. FIGS. 25 and 26 are a perspective view and cross-sectional view of a lower body 214 of the sixth locking element. The locking element 210 further includes a contact plate 217 that is seated in a U-shaped seat 219 of the lower body 214 and an inverted U-shaped cap 218 that fits over the U-shaped seat 219. The cartridge 212 has a pair of posts 220 each with an upper outer tapered surface 225 and a ledge 223. The lower body 214 has a hollow nose 227 comprising a pair of rigid arms 216 and a pair of pivoting lever arms 221. The levers 221 each have a button 224 and an inside ledge 226. When the cartridge posts 220 are in the lower body 214, the ledges 226 abut the tapered upper surface 225 of the posts 220.

When the buttons are squeezed together, the cartridge is ejected. As the buttons force the lever edges 226 against the tapered surface 225, the posts 220 deflect inwardly and are released from a ledge 222 on the lever arms of the lower body. The arms 221 and buttons 224 abut but do not latch the posts of the cartridge. Stops in the hollow lower body prevent the posts and cartridge from rotating. Extending inward from the rigid arms 216, are ribs 228 to support a central shaft 229 for the contact pin and the ledges 222 that engage the flat ledge 223 on the post of the cartridge. The ledges 222 may form a rigid ring below the lower inner edge of the buttons 224. The posts deflect inward as they slide up into the nose 227. The flat ledges 223 of the posts snap over and latch onto the ledge ring 222 of the nose.

Figure 27:
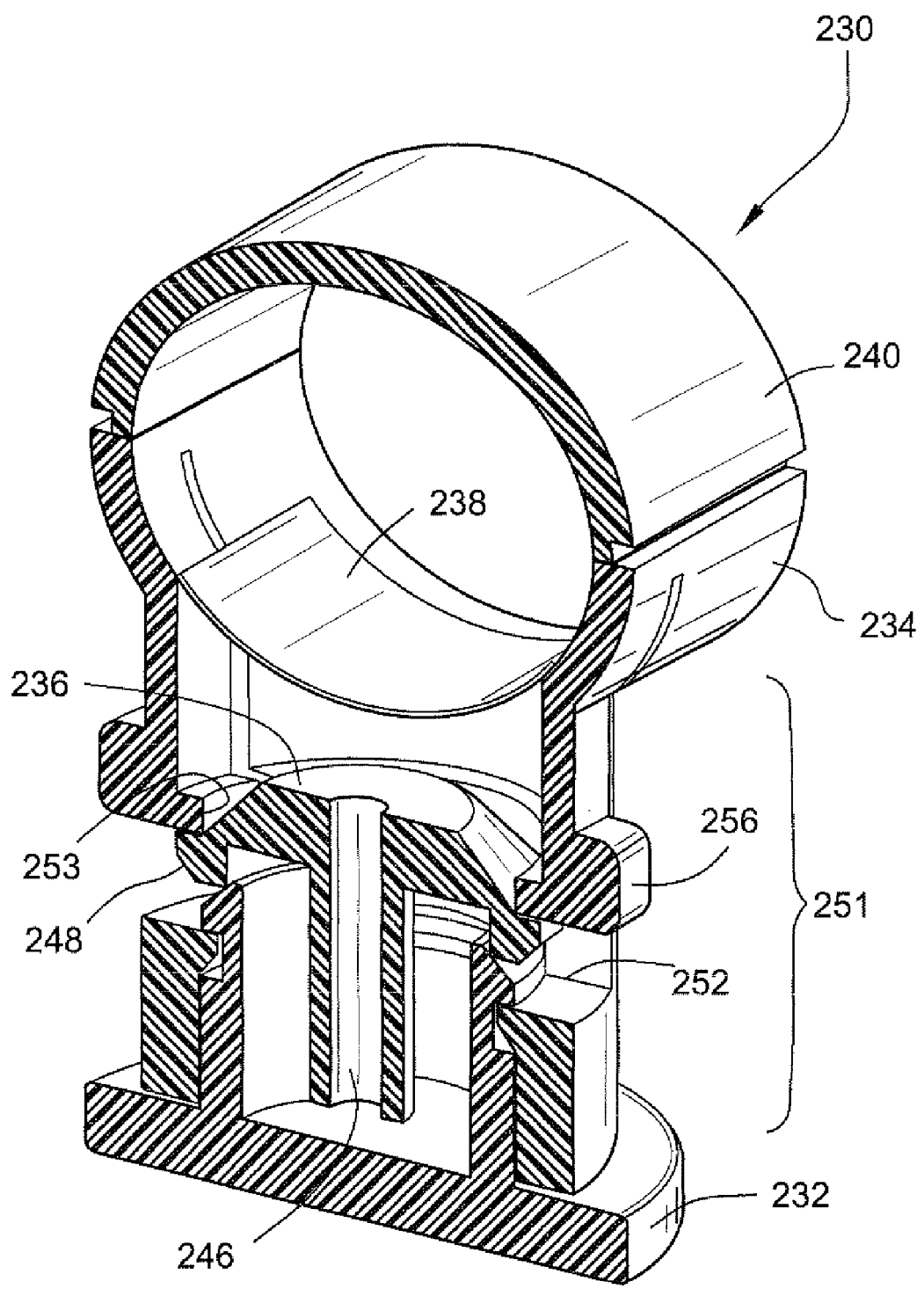
FIGS. 27 and 28 are a cross-sectional view and an exploded view, respectively, of a cartridge locking element and cartridge for a seventh embodiment of the device.
Figure 28:
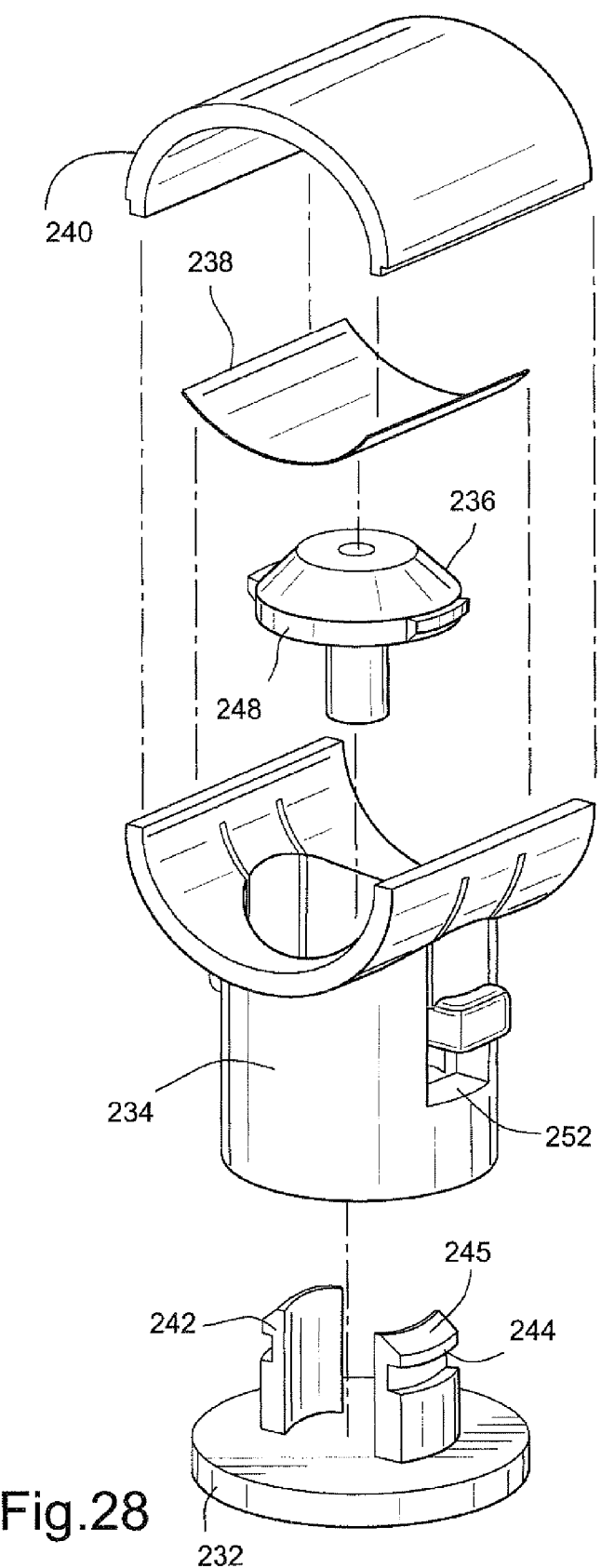
Figure 29:
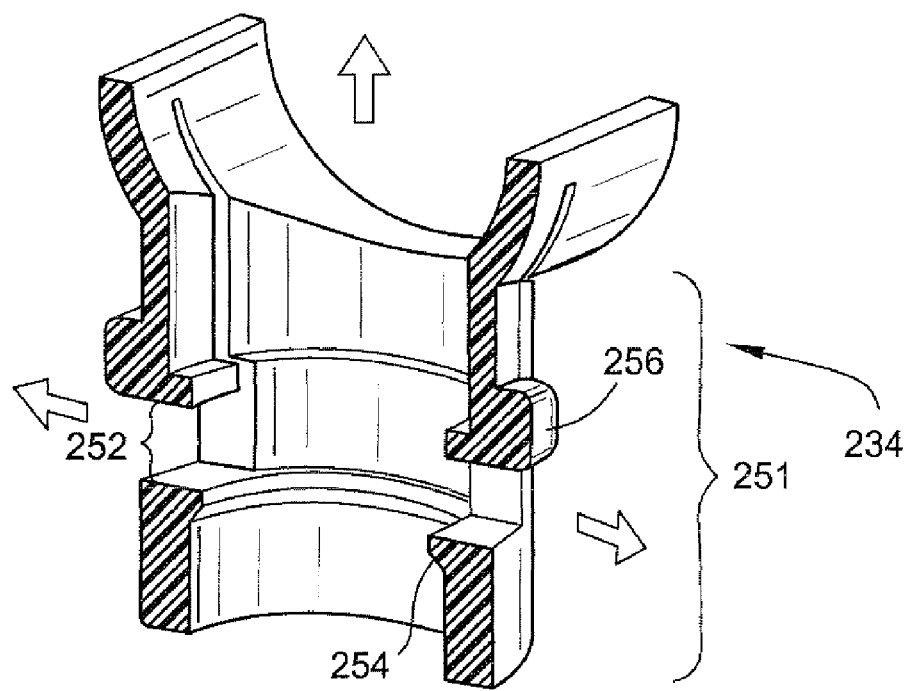
FIG. 29 is a cross-sectional view of the lower body of an locking element shown in FIGS. 27 and 28.
Figure 30:
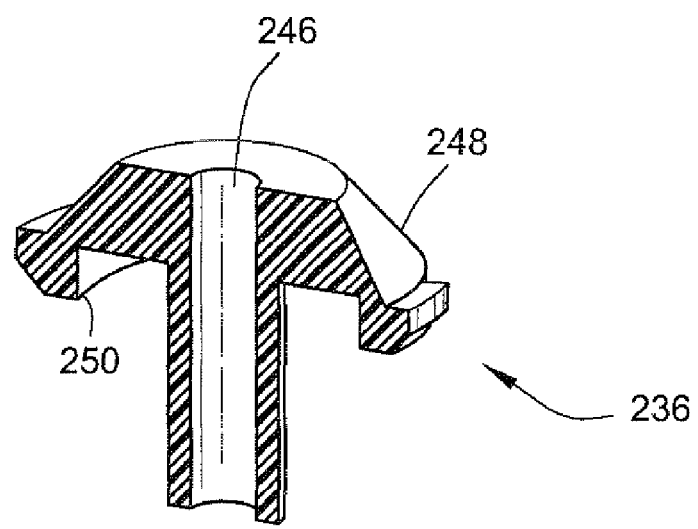
FIG. 30 is a cross-sectional view of an ejector and pin support for use with the locking element shown in FIGS. 27 to 29.

FIGS. 27 and 28 are a cross-sectional view and an exploded view, respectively, of a further locking element 230 and cartridge 232. The cartridge includes an active electrode and medicament matrix that are not shown. FIG. 29 is a cross-sectional view of a lower body 234 of the locking element 230. FIG. 30 is a cross-sectional view of an ejector and pin support 236. A contact plate 238 is seated in a U-shaped portion of the lower body. An inverted U-shaped upper body 240 fits over the contact plate and U-shaped portion of the lower body which together form a finger aperture. The posts 242 of the cartridge 232 include an outer slot 244 that forms a ledge to engage the lower body and an upper tapered surface 245 that receives a bearing force to bend the posts inward as the cartridge is inserted and removed from the lower body.

The ejector and pin support 236 includes a hollow center shaft 246 to receive a contact pin. An annular cap 248 on the support 236 has an outer frustoconical bearing surface and an inner annular rim 250. The support 236 is seated in a hollow cylindrical section of the nose 251 of the lower body 234. The hollow nose has a slot 252 to receive the cap 248 and the upper section of the posts 242 of the cartridge. The cartridge is inserted into the nose such that the posts 242 are deflected by a beveled annular surface 254 in the hollow section of the lower body. The slots 244 on the posts snap over the annular surface 254 in the nose 251.

The rim 250 of the cap 248 abuts the tapered upper surfaces 245 of the posts 242 when the cap and posts of the cartridge are in the slot 252 of the nose 251. The frustoconical upper surfaces of the cap engage an inside surface 253 of the buttons 256. The buttons are on the arms extending downwardly from the U-shaped section of the lower body. As the buttons are squeezed together, the buttons force the cap downward. The rim of the downwardly sliding cap forces inward and downward the posts on the cartridge. In this way, the cartridge is ejected.

Figure 31:
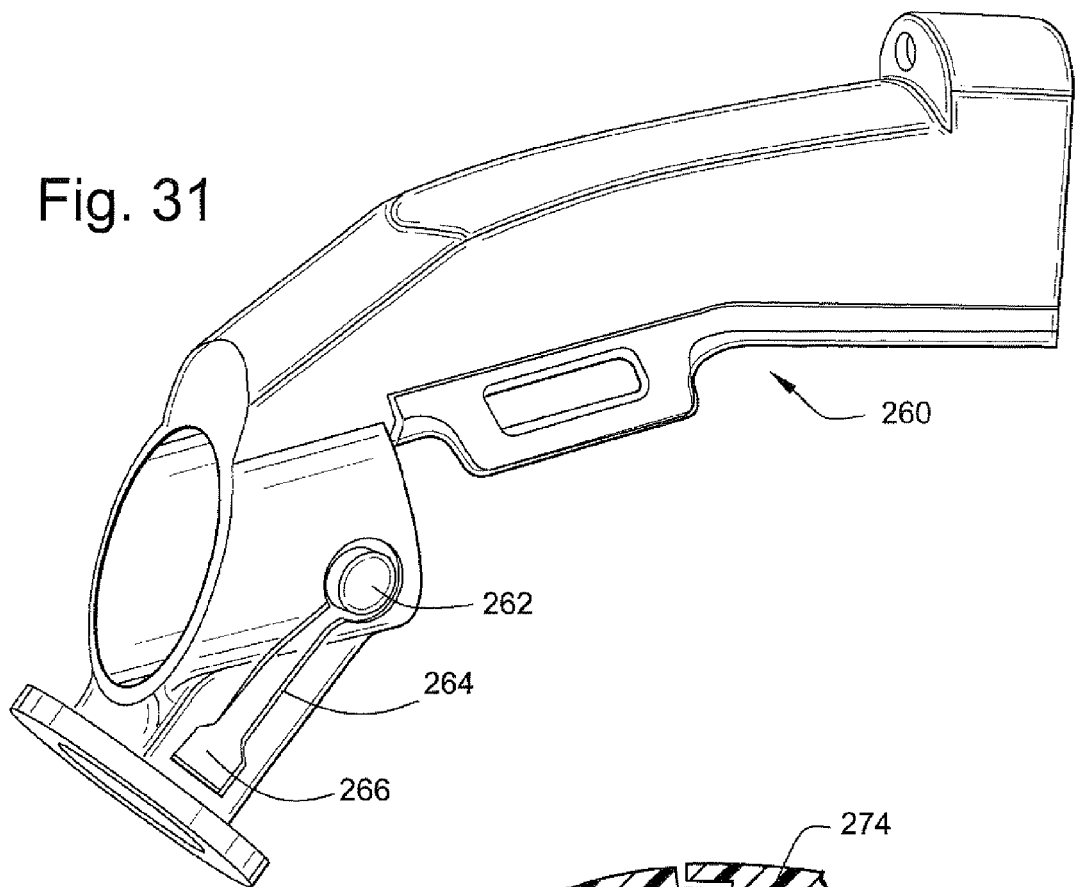
FIG. 31 is a side view of an eighth embodiment of the device having a housing with a cartridge locking element and a cartridge.

FIG. 31 is a side view of another embodiment of the housing 260 having levered ejection buttons 262. As the buttons are pressed inward, the arms with the buttons pivot about a pivot point 264 between the buttons and latch ends 266 of the arms. Because of the pivot, the latch ends swing outward and release the posts of the cartridge (not shown). The buttons and lever arms with latch ends can be molded with the housing to form a unitary plastic housing.

Figure 32:
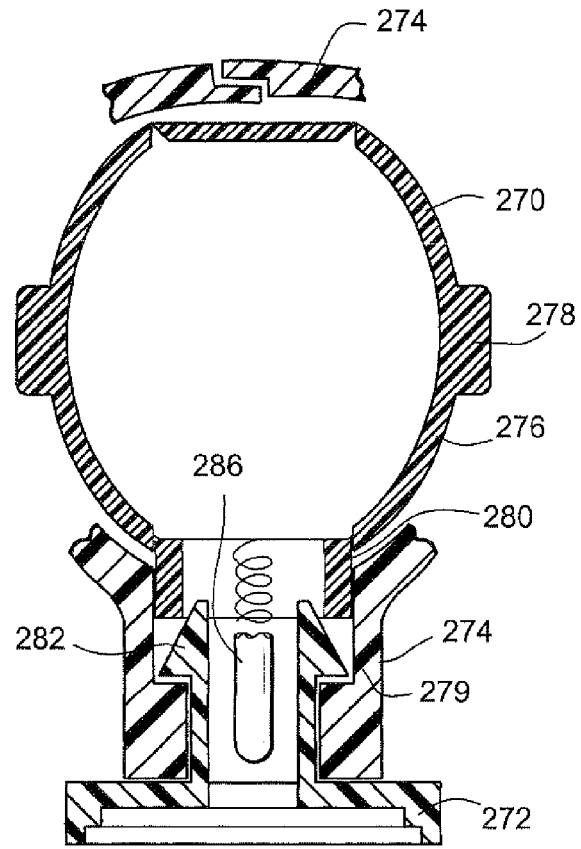
FIGS. 32 and 33 are a front, cross-sectional view and an exploded view, respectively, of a cartridge locking element and cartridge for a ninth embodiment of the device.
Figure 33:
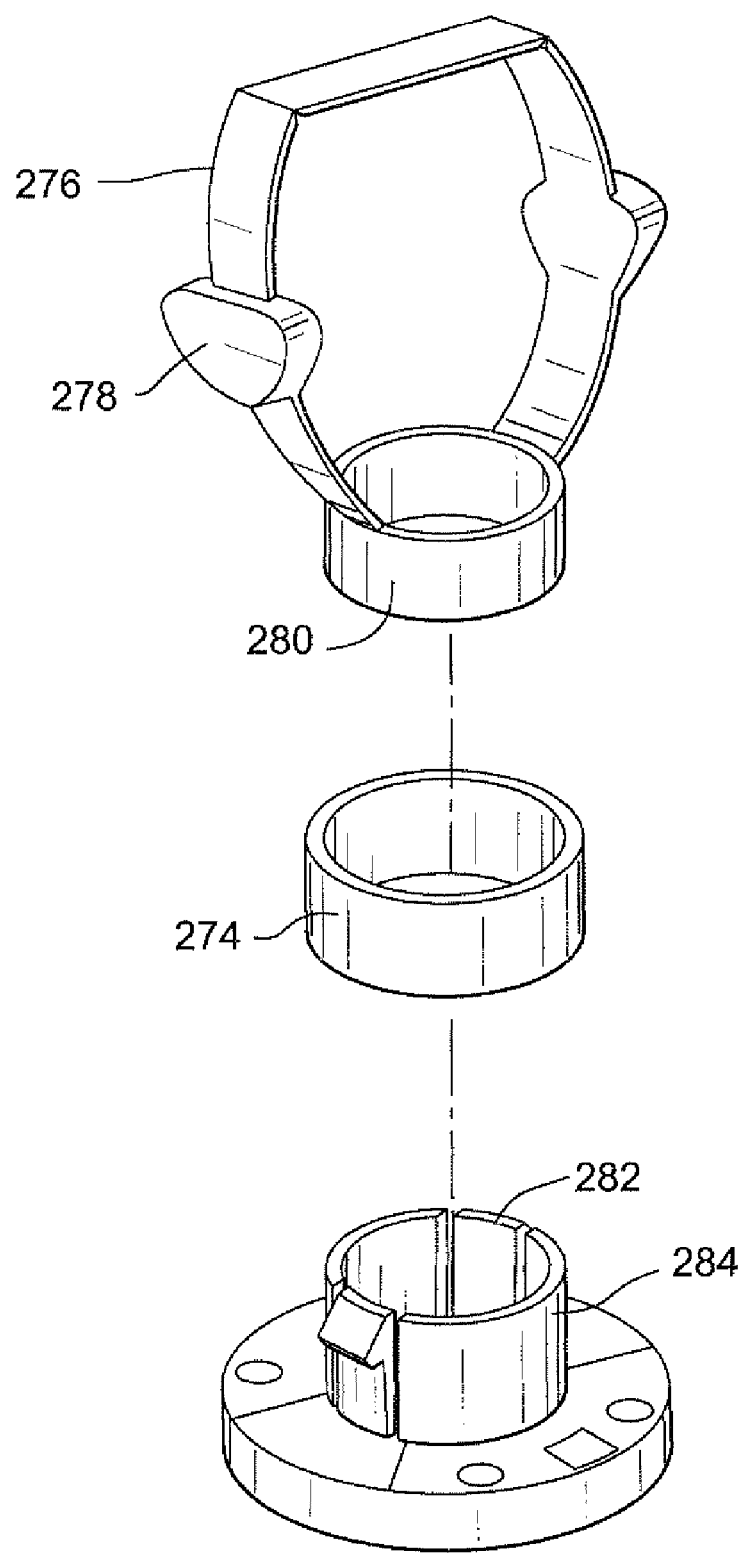
Figure 34:
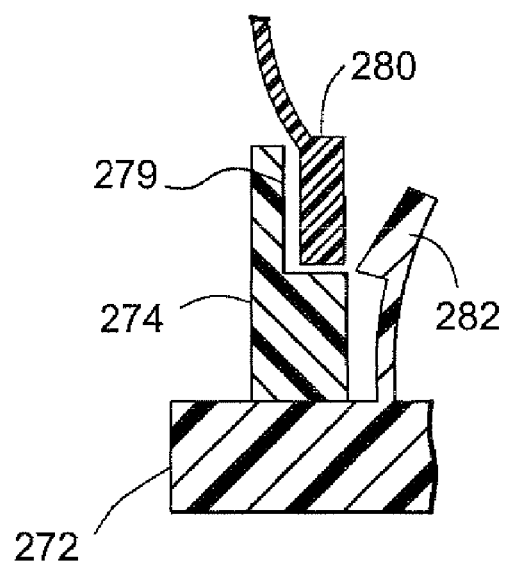
FIGS. 34 and 35 are fragmented cross-sectional views of the cartridge attachment and cartridge shown in FIGS. 32 and 33.
Figure 35:
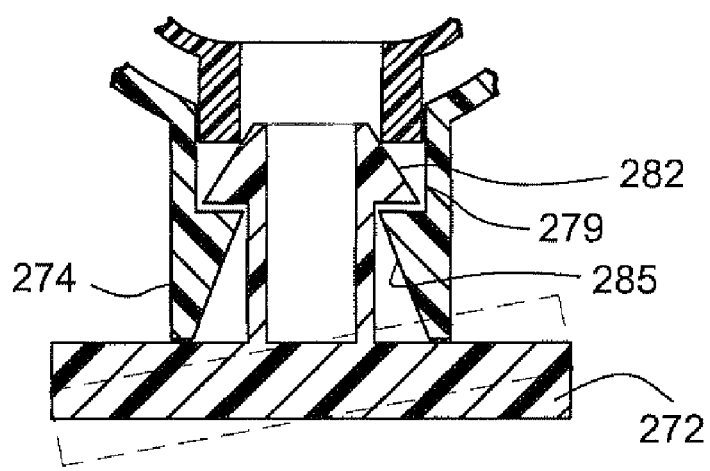

FIG. 32 is a cross-section view of an locking element 270 for attaching a cartridge head 272 to a housing 274. The cartridge includes an active electrode and medicament matrix, which are not shown. FIG. 32 is a cross-sectional view of a spring clip 276, collar 280, cartridge and a portion of the housing 274. FIG. 33 is an exploded view of the spring clip, collar and cartridge. FIG. 34 is a fragmented view of the spring clip, collar and cartridge and FIG. 35 is a fragmented view of the spring clip, collar and cartridge showing the collar with a tapered inside surface.

The spring clip 276 is formed of a flat section of a deformable material, e.g., plastic sheet. The spring clip includes a bulbous section with buttons 278 and a collar 280. The spring clip fits in a distal end of the housing 274 such that the buttons are exposed through the housing. The collar 280 is seated in an annular recess 279 in the nose of the housing. Seated below the collar 280 are the tapered ends of the posts 282 of the cartridge head. The posts may deform easily. The distal end of the housing may be a hollow cylinder 274 that fits snugly around the posts (note that 274 is representative of the entire housing 260). The cartridge head includes semi-cylindrical walls 284 on either side of the posts 282. The walls provide a bearing support for the cartridge in the hollow housing cylinder 274. A contact pin 286 extends axially through the collar and posts to provide an electrical connection between the power supply in the housing and the active electrode in the cartridge.

To eject the cartridge, the buttons 278 are squeezed together to cause the collar 280 to slide downward against the tapered ends of the posts 282. As the posts to deflect inward, they clear the ledge of the recess 279 in the housing 274 and are released from the cartridge. To facilitate insertion of the cartridge, the inner cylindrical wall of the nose may be tapered to engage the tapered surface of the posts 282. The tapered wall 285 (FIG. 35) allows the cartridge to pivot when seated in the nose of the housing. The tapered inner wall of the nose allows the cartridge to pivot a few degrees to avoid ejection of the cartridge when removing the lid and to facilitate contact between the cartridge and skin.

The invention(s) has been described in connection with what is presently considered to be the most practical and preferred embodiment(s). It is to be understood that the invention is not to be limited to the disclosed embodiments and that the invention covers variations of the disclosed embodiments such as where features of one embodiment are combined with features of another embodiment to form a further embodiment of the invention. The invention is intended to cover various modifications and equivalent arrangements included within the spirit and scope of the appended claims.

We claim:

1. An electrokinetic delivery system for administration of a medicament to a treatment site on a human individual, the delivery system comprising:
a cartridge applicator device shaped in part to conform to at least a portion of the undersurface of a digit of the individual and including a retainer for releasably securing the applicator device to the digit, a power source or coupling thereto, and a tactile electrode positioned on a portion of the cartridge applicator device to contact at least a portion of the undersurface of the individual's digit;
a cartridge including a first side for supporting a medicament, a second side, opposite to the first side, facing the applicator device when the cartridge is secured to the applicator device, and an active electrode accessible through the second side from the first side, wherein the active electrode is in electrical contact with said medicament and said power source when said cartridge is secured to the applicator device, such that the cartridge is positioned between the treatment site and the undersurface of the individual's digit when the undersurface of the individual's digit is in contact with the tactile electrode;
whereby, upon application of the active electrode to the treatment site with a medicament interposed between said active electrode and the treatment site and completion of an electrical circuit through the active electrode, the medicament or a conductive carrier therefor, the treatment site, the individual's body, the tactile electrode and the power source, said device causes an electrical current to flow for electrokinetically driving the medicament from the cartridge into the treatment site, and
a locking element carried by one of the cartridge applicator device and the second side of the cartridge and engaged with a locking surface on another one of said device and the second side of the cartridge allows for slight pivoting when engaged, said locking element is movable to release the securement between the cartridge applicator device and the cartridge enabling release of the cartridge from the device.

2. An electrokinetic delivery system according to claim 1 wherein said locking element includes a rim having an underside ledge on the cartridge and a deformable latch arm having the another surface of the device, wherein the latch arm deforms while sliding into the rim and thereafter latches to the rim.

3. An electrokinetic delivery system according to claim 2 wherein said locking element includes a post having an underside ledge serving as the locking surface on the cartridge and a deformable latch arm having the another surface of the device, wherein the latch arm deforms while sliding into the rim and thereafter latches to the rim.

4. An electrokinetic delivery system according to claim 3 wherein said post is a pair of posts on opposite sides of an opening in the cartridge which exposes the active electrode.

5. An electrokinetic delivery system according to claim 4 where the underside ledge of each post faces away form the opening in the cartridge.

6. An electrokinetic delivery system according to claim 3 wherein said post and deformable latch arm cooperate to releasable lock the cartridge in the device.

7. An electrokinetic delivery system according to claim 1 wherein said second side of the cartridge and said device have co-operable surfaces at least one of which is deformable to abut against the other surface to forcibly eject the cartridge from the device.

8. An electrokinetic delivery system according to claim 7 wherein said co-operable elements include a pair of resilient posts carried by said one of the second side of the cartridge and the device, and tapered surfaces carried by said another of the second side of cartridge and the device.

9. An electrokinetic delivery system according to claim 8 wherein said posts engage respective locking surfaces on said another of the second side of the cartridge and said device.

10. An electrokinetic delivery system according to claim 7 wherein at least one of said co-operable elements is moveable to allow an insertion of the cartridge into the device.

11. An electrokinetic delivery system according to claim 1 wherein the locking element includes at least one post with a locking flat surface, and the post engages the another one of said device and the second side of the cartridge.

12. An electrokinetic delivery system according to claim 11 wherein said another of said device and second side of the cartridge includes a surface co-operable with said post.

13. An electrokinetic delivery system according to claim 1 wherein said cartridge includes a pair of resilient posts upstanding on the second side, and said device includes a pair of locking surfaces and a pair of tapered surfaces, said posts engaging said locking surfaces to secure the cartridge to the device and are moveable against a bias to engage the pair of tapered surfaces enabling the cartridge to be forcibly ejected from the device.

14. An electrokinetic delivery system according to claim 13 including a pair of push buttons on respective sides of the device for moving the posts against the bias to forcibly eject the cartridge from the device.

15. An electrokinetic delivery system according to claim 1 wherein the locking element includes a weakness preventing reuse of said cartridge upon release of the cartridge from the device.

16. An electrokinetic delivery system for administration of a medicament to a treatment site on a human individual, said system comprising:
an applicator shaped in part to conform to at least a portion of the undersurface of a digit of an individual, including a power source or coupling thereto, and a tactile electrode positioned on a portion of the cartridge applicator device to contact at least a portion of the undersurface of the individual's digit;
a cartridge having a first surface to receive a medicament matrix and a second surface facing the applicator when the cartridge is releasably secured to the applicator, such that the cartridge is positioned between the treatment site and the undersurface of the individual's digit when the undersurface of the individual's digit is in contact with the tactile electrode;
a locking element carried by one of the device and said second surface of the cartridge and engaged with a locking surface on another of said device and said second surface of the cartridge allows for slight pivoting when engaged, said element being movable thereof to release the securement between the device and the cartridge enabling release of the cartridge from the device, said another of said device and said second surface of the cartridge includes an actuating surface co-operable with said element enabling a bias of said element to forcibly eject the cartridge from the device;

wherein said cartridge includes an active electrode extending through the second surface and to a medicament matrix, said active electrode in electrical contact with said power source or coupling thereto when said cartridge is secured to the device whereby, upon application of the active electrode to the treatment site with a medicament interposed between said active electrode and the treatment site and completion of an electrical circuit through the active electrode, the medicament or a conductive carrier therefor, the treatment site, the individual's body, the tactile electrode and the power source, said delivery system causes an electrical circuit to flow for electrokinetically driving the medicament from the cartridge into the treatment site.

17. A system according to claim 16 wherein said element includes a resilient post carried by said one of said second surface of the cartridge and the device and a tapered surface carried by said another of the cartridge and the device enabling forcible ejection of the cartridge from the device.

18. A system according to claim 17 wherein said post engages a locking surface on said another of said second surface of the cartridge and said device to secure the cartridge and device to one another and engages the tapered surface carried by said another of said second surface of the cartridge and said device to forcibly eject the cartridge from the device upon disengagement from the locking surface.

19. A system according to claim 18, wherein said inter-engaging element is moveable in response to relative displacement of the cartridge and device toward one another to engage the other of said element enabling the cartridge and the device for releasable securement to one another.

* * * * *